US009175312B2

(12) United States Patent
Chen

(10) Patent No.: US 9,175,312 B2
(45) Date of Patent: Nov. 3, 2015

(54) VECTORS HARBORING TOXIC GENES, METHODS AND USES THEREFOR

(71) Applicant: Haifeng Chen, Piedmont, CA (US)

(72) Inventor: Haifeng Chen, Piedmont, CA (US)

(73) Assignee: Virovek Incorporation, Hayward, CA (US)

( * ) Notice: Subject to any disclaimer, the term of this patent is extended or adjusted under 35 U.S.C. 154(b) by 0 days.

(21) Appl. No.: 13/982,530

(22) PCT Filed: Oct. 16, 2012

(86) PCT No.: PCT/US2012/060441
§ 371 (c)(1),
(2) Date: Jul. 30, 2013

(87) PCT Pub. No.: WO2013/085624
PCT Pub. Date: Jun. 13, 2013

(65) Prior Publication Data
US 2014/0296324 A1 Oct. 2, 2014

Related U.S. Application Data

(60) Provisional application No. 61/568,595, filed on Dec. 8, 2011, provisional application No. 61/618,689, filed on Mar. 31, 2012.

(51) Int. Cl.
| | |
|---|---|
| *C07H 21/00* | (2006.01) |
| *C12N 15/86* | (2006.01) |
| *A61K 31/7088* | (2006.01) |
| *C07K 14/34* | (2006.01) |
| *C07K 14/21* | (2006.01) |
| *C12N 9/22* | (2006.01) |
| *C12N 9/24* | (2006.01) |
| *A61K 48/00* | (2006.01) |

(52) U.S. Cl.
CPC ........... *C12N 15/86* (2013.01); *A61K 31/7088* (2013.01); *C07K 14/21* (2013.01); *C07K 14/34* (2013.01); *C12N 9/22* (2013.01); *C12N 9/2497* (2013.01); *A61K 48/00* (2013.01); *C12N 2710/14043* (2013.01); *C12N 2710/14052* (2013.01); *C12N 2750/14143* (2013.01); *C12N 2750/14152* (2013.01); *C12N 2799/026* (2013.01); *C12N 2830/42* (2013.01); *C12N 2840/005* (2013.01); *C12N 2840/102* (2013.01); *C12N 2840/44* (2013.01); *C12N 2840/85* (2013.01)

(58) Field of Classification Search
None
See application file for complete search history.

(56) References Cited

U.S. PATENT DOCUMENTS

| | | | |
|---|---|---|---|
| 5,994,128 | A | 11/1999 | Fallaux et al. |
| 6,033,908 | A | 3/2000 | Bout et al. |
| 6,204,059 | B1 | 3/2001 | Samulski et al. |
| 6,265,212 | B1 | 7/2001 | Fallaux et al. |
| 6,306,652 | B1 | 10/2001 | Fallaux et al. |
| 6,723,551 | B2 | 4/2004 | Kotin et al. |
| 7,582,290 | B2 | 9/2009 | Rodriguez et al. |
| 2003/0148506 | A1 | 8/2003 | Kotin et al. |
| 2009/0203071 | A1 | 8/2009 | Chen |

FOREIGN PATENT DOCUMENTS

| | | |
|---|---|---|
| WO | WO/99/03981 | 1/1999 |

OTHER PUBLICATIONS

Urabe, 2002, Human Gene Therapy, 13:1935-1943.*
Chen, 2008, Molecular Therapy, 16:924-930.*
Katz, 1990, Molecular and Cellular Biology, 10:696-704.*
Jeang (1987, J Virol, 61:1761-1764).*
Ellerby, H. M., et al. "Anti-cancer activity of targeted pro-apoptotic peptides." Nat. Med. 5(9):1032-8. (1999).
Huajie Zhang, et al., Research Progress of Diphtheriatoxin Antitumor. Infectious Disease Information vol. 16. No. 2. Dec. 31, 2003.
Denning, C., et al. "Bystander Effects of Different Enzyme-Prodrug Systems for Cancer Gene Therapy Depend on Different Pathways for Intercellular Transfer of Toxic Metabolites, a Factor That Will Govern Clinical Choice of Appropriate Regimes." Hum. Gene Ther. 8(15): 1825-1835 (1997).
Edelweiss, E., et al. "Barnase as a new therapeutic agent triggering apoptosis in human cancer cells." PLoS ONE. 3: e2434. (2008).
Ellerby, H.M., et al. "Anti-cancer activity of targeted pro-apoptotic peptides." Nat. Med. 5(9):1032-8. (1999).
Gu, J., et al. "hTERT promoter induces tumor-specific Bax gene expression and cell killing in syngenic mouse tumor model and prevents systemic toxicity." Gene. Ther. 9(1):30-7. (2002).
Keyvani, K., et al. "Tetracycline-controlled expression but not toxicity of an attenuated diphtheria toxin mutant." Life. Sci. 64:1719-1724. (1999).

(Continued)

*Primary Examiner* — Valarie Bertoglio
(74) *Attorney, Agent, or Firm* — Saul L. Zackson; Zackson Law LLC

(57) ABSTRACT

The present disclosure describes nucleic acids, and viruses comprising such nucleic acids, for growing a toxic gene in an insect cell. These nucleic acids comprise a sequence encoding a toxic polypeptide, and an intron that interrupts the sequence, whereby the intron is spliced in mammalian cells but not in insect cells. Infection of mammalian cells but not insect cells with the nucleic acids or viruses can lead to expression of toxic levels of the toxic polypeptide in mammalian cells but not in insect cells. Viruses, such as an AAV or a baculovirus comprising a nucleic acid can be grown in insect cell lines in vitro and can be administered to a subject in need of therapy, such as a subject in need of cancer therapy.

26 Claims, 23 Drawing Sheets

(56) References Cited

OTHER PUBLICATIONS

Kohlschutter, J., et al. "Novel cytotoxic vectors based on adeno-associated virus." Toxins. 2:2754-2768. (2010).

Maxwell, I.H., et al. "Regulated Expression of a Diphtheria Toxin A-Chain Gene Transfected Into Human Cells: Possible Strategy for Inducing Cancer Cell Suicide." Cancer Research. 46:4660-4664. (1986).

Maxwell, F., et al. "Cloning, sequence determination, and expression in transfected cells of the coding sequence for the tox 176 attenuated diphtheria toxin A chain." Mol. Cell Biol. 7:1576-1579. (1987).

Paulus, W., et al. "Regulated expression of the diphtheria toxin A gene in human glioma cells using prokaryotic transcriptional control elements." J. Neurosurg. 87:89-95. (1997).

Robinson, D.F., et al. "Suppression of single and double nonsense mutations introduced into the diphtheria toxin A-chain gene: a potential binary system for toxin gene therapy." Hum. Gene Ther. 6:137-143. (1995).

Rodriguez, R., et al. "Urologic applications of gene therapy." Urology. 54:401-406. (1999).

Wang, C.Y., et al. "Recombinant baculovirus containing the diphtheria toxin A gene for malignant glioma therapy." Cancer Res. 66:5798-5806. (2006).

Yamaizumi, M. et al. "One molecule of diphtheria toxin fragment A introduced into a cell can kill the cell." Cell. 15: 245-250. (1978).

Zhu, Z.B., et al. "Transcriptional targeting of tumors with a novel tumor-specific survivin promoter." Cancer. Gene. Ther. Apr;11(4):256-62. (2004).

Zhu, Z.B., et al. "Transcriptional targeting of adenoviral vector through the CXCR4 tumor-specific promoter." Gene Ther. Apr;11(7):645-8. (2004).

Moran Y et al: "Intron Retention as a 1-16 Posttranscriptional Regulatory Mechanism of Neurotoxin Expression at Early Life Stages of the Starlet Anemone Nematostella vectensis". Journal of Molecular Biology. Academic Press. United Kingdom. vol. 380. No. 3. Jul. 11, 2008•pp. 437-443. XP022736352. ISSN: 0022-2836. DOI: 10.1016/J.JMB.2008.05.011.

Haifeng Chen: "Exploiting the Intron-splicing Mechanism of Insect Cells to Produce Viral Vectors Harboring Toxic Genes for Suicide Gene Therapy". Molecular Therapy—Nucleic Acids. vol. 1 • 1. No. 11. Nov. 27, 2012. p. e57. XP055195248. DOI: 10.1038/mtna.2012.48.

\* cited by examiner

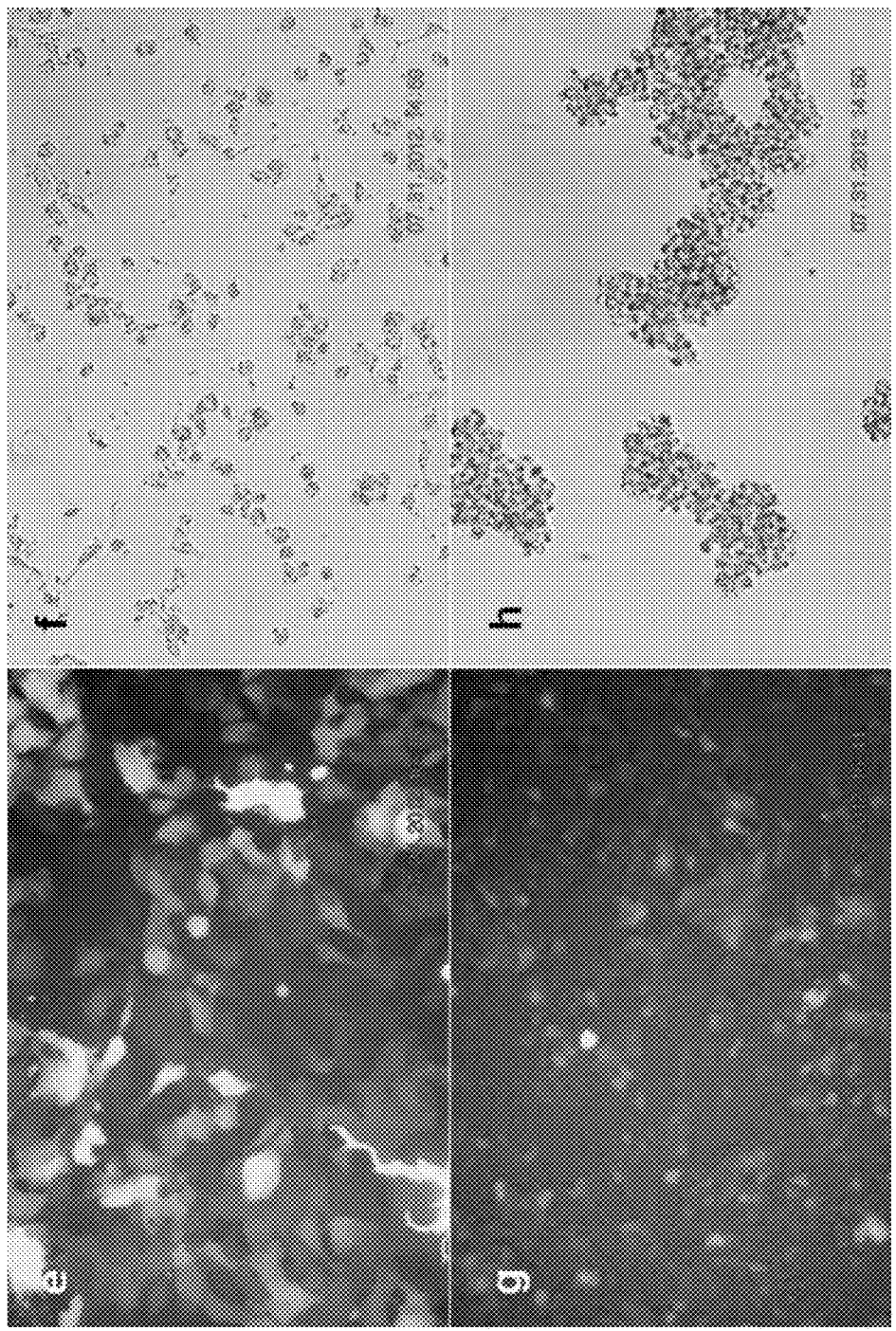

SEQUENCE LISTING

```
<160> NUMBER OF SEQ ID NOS: 41

<210> SEQ ID NO 1
<211> LENGTH: 144
<212> TYPE: DNA
<213> ORGANISM: Simian virus 40

<400> SEQUENCE: 1
catggcccaa cttgtttatt gcagcttata atggttacaa ataaagcaat agcatcacaa      60
atttcacaaa taaagcattt ttttcactgc attctagttg tggtttgtcc aaactcatca     120
atgtatctta tcatgtctgg atct                                            144

<210> SEQ ID NO 2
```

-continued

<211> LENGTH: 20
<212> TYPE: DNA
<213> ORGANISM: Corynebacterium diphtheriae virus

<400> SEQUENCE: 2
gattatgatc actagtcgag 20

<210> SEQ ID NO 3
<211> LENGTH: 30
<212> TYPE: DNA
<213> ORGANISM: Artificial Sequence
<220> FEATURE:
<223> OTHER INFORMATION: DT-A with human growth hormone intron sequence

<400> SEQUENCE: 3
gggcgcttac ctttttgaat ggaatctaca 30

<210> SEQ ID NO 4
<211> LENGTH: 30
<212> TYPE: DNA
<213> ORGANISM: Homo sapiens

<400> SEQUENCE: 4
attcaaaaag gtaagcgccc ctaaaatccc 30

<210> SEQ ID NO 5
<211> LENGTH: 30
<212> TYPE: DNA
<213> ORGANISM: Homo sapiens

<400> SEQUENCE: 5
ttttgtatac ctggggagaa accagagggc 30

<210> SEQ ID NO 6
<211> LENGTH: 20
<212> TYPE: DNA
<213> ORGANISM: Artificial Sequence
<220> FEATURE:
<223> OTHER INFORMATION: overlapping DT-A and HGH intron PCR amplification

<400> SEQUENCE: 6
gattatgatc actagtcgag 20

<210> SEQ ID NO 7
<211> LENGTH: 30
<212> TYPE: DNA
<213> ORGANISM: Artificial Sequence
<220> FEATURE:
<223> OTHER INFORMATION: DT-A and HGH intron overlapping PCR amplification

<400> SEQUENCE: 7
ttttgtatac ctggggagaa accagagggc 30

<210> SEQ ID NO 8
<211> LENGTH: 1683
<212> TYPE: DNA
<213> ORGANISM: Corynebacterium diphtheriae virus

<400> SEQUENCE: 8
gtgagcagaa aactgtttgc gtcaatctta ataggggcgc tactggggat aggggcccca 60
ccttcagccc atgcaggcgc tgatgatgtt gttgattctt ctaaatcttt tgtgatggaa 120
aacttttctt cgtaccacgg gactaaacct ggttatgtag attccattca aaaaggtata 180

```
caaaagccaa aatctggtac acaaggaaat tatgacgatg attggaaagg gttttatagt      240
accgacaata aatacgacgc tgcgggatac tctgtagata atgaaaaccc gctctctgga      300
aaagctggag gcgtggtcaa agtgacgtat ccaggactga cgaaggttct cgcactaaaa      360
gtggataatg ccgaaactat taagaaagag ttaggtttaa gtctcactga accgttgatg      420
gagcaagtcg gaacggaaga gtttatcaaa aggttcggtg atggtgcttc gcgtgtagtg      480
ctcagccttc ccttcgctga ggggagttct agcgttgaat atattaataa ctgggaacag      540
gcgaaagcgt taagcgtaga acttgagatt aattttgaaa cccgtggaaa acgtggccaa      600
gatgcgatgt atgagtatat ggctcaagcc tgtgcaggaa atcgtgtcag gcgatcagta      660
ggtagctcat tgtcatgcat aaatcttgat tgggatgtca aagggataaa aactaagaca      720
aagatagagt ctttgaaaga gcatggccct atcaaaaata aaatgagcga aagtcccaat      780
aaaacagtat ctgaggaaaa agctaaacaa tacctagaag aatttcatca aacggcatta      840
gagcatcctg aattgtcaga acttaaaacc gttactggga ccaatcctgt attcgctggg      900
gctaactatg cggcgtgggc agtaaacgtt gcgcaagtta tcgatagcga aacagctgat      960
aatttggaaa agacaactgc tgctctttcg atacttcctg gtatcggtag cgtaatgggc     1020
attgcagacg gtgccgttca ccacaataca gaagagatag tggcacaatc aatagcttta     1080
tcgtctttaa tggttgctca agctattcca ttggtaggag agctagttga tattggtttc     1140
gctgcatata attttgtaga gagtattatc aattatttc aagtagttca taattcgtat      1200
aatcgtcccg cgtattctcc ggggcataaa acgcaaccat tcttcatga cgggtatgct      1260 gtcagttgga acactgttga agattcgata atccgaactg gttttcaagg ggagagtggg     1320
cacgacataa aaattactgc tgaaaatacc ccgcttccaa tcgcgggtgt cctactaccg     1380
actattcctg gaaagctgga cgttaataag tccaagactc atatttccgt aaatggtcgg     1440
aaaataagga tgcgttgcag agctatagac ggtgatgtaa cttttttgtcg ccctaaatct     1500 cctgtttatg ttggtaatgg tgtgcatgcg aatcttcacg tggcatttca cagaagcagc     1560
tcggagaaaa ttcattctaa tgaaatttcg tcggattcca taggcgttct tgggtaccag     1620
aaaacagtag atcacaccaa ggttaattct aagctatcgc tatttttga aatcaaaagc      1680 tga                                                                   1683
```

<210> SEQ ID NO 9
<211> LENGTH: 33
<212> TYPE: DNA
<213> ORGANISM: Artificial Sequence
<220> FEATURE:
<223> OTHER INFORMATION: barnase coding sequence amplified from plasmid
pF1A-T7

<400> SEQUENCE: 9

```
cccgaattcg ccaccatggc acaggttatc aac                                     33
```

<210> SEQ ID NO 10
<211> LENGTH: 30
<212> TYPE: DNA
<213> ORGANISM: Artificial Sequence
<220> FEATURE:
<223> OTHER INFORMATION: barnase coding sequence amplified from plasmid
pF1A-T7

<400> SEQUENCE: 10

```
tgctcaccat tctgattttt gtaaaggtct                                         30
```

<210> SEQ ID NO 11
<211> LENGTH: 30
<212> TYPE: DNA
<213> ORGANISM: Artificial Sequence
<220> FEATURE:
<223> OTHER INFORMATION: GFP coding sequence amplified from pFB-GFP
      plasmid

<400> SEQUENCE: 11
caaaaatcag aatggtgagc aagggcgagg                                     30

<210> SEQ ID NO 12
<211> LENGTH: 32
<212> TYPE: DNA
<213> ORGANISM: Artificial Sequence
<220> FEATURE:
<223> OTHER INFORMATION: GFP coding sequence amplified from pFB-GFP
      plasmid

<400> SEQUENCE: 12 gggggggtacc tcattacttg tacagctcgt cc                                 32

<210> SEQ ID NO 13
<211> LENGTH: 33
<212> TYPE: DNA
<213> ORGANISM: Artificial Sequence
<220> FEATURE:
<223> OTHER INFORMATION: PCR to fuse Barnase coding sequence with GFP
      coding sequence

<400> SEQUENCE: 13
cccgaattcg ccaccatggc acaggttatc aac                                 33

<210> SEQ ID NO 14
<211> LENGTH: 32
<212> TYPE: DNA
<213> ORGANISM: Artificial Sequence
<220> FEATURE:
<223> OTHER INFORMATION: PCR to fuse barnase coding sequence with GFP

<400> SEQUENCE: 14 gggggggtacc tcattacttg tacagctcgt cc                                 32

<210> SEQ ID NO 15
<211> LENGTH: 832
<212> TYPE: DNA
<213> ORGANISM: Bacillus amyloliquefaciens

<400> SEQUENCE: 15
ctggaaaacg tcacattgct tccgcatatc gggtcagcaa cggctaaaat ccgcttgaat     60
atgttcacac aagccgctca aacatgatt gacgccgtat acggaagaac gccgaaaaac    120
cttactaagg aatttcaata agaagaaaaa tcccggttgg ttcagccggg gtttattttt    180
cgctagataa aaagtactat ttttaaattc tttctattcc tttctttcgt tgctgataca    240
atgaaaagga atcagcttca catgatgaaa atggaggta ttgctttgaa aaacgattta    300
tcgtggattt ccgtttgttt actggtgctt gtctccgcgg cggggatgct gttttcaaca    360
gctgccaaaa cggaaacatc ttctcacaag gcacacacag aagcacaggt tatcaacacg    420
tttgacgggg ttgcggatta tcttcagaca tatcataagc tacctgataa ttacattaca    480
aaatcagaag cacaagccct cggctgggtg gcatcaaaag ggaaccttgc agacgtcgct    540
ccggggaaaa gcatcggcgg agacatcttc tcaaacaggg aaggcaaact cccgggcaaa    600

```
agcggacgaa catggcgtga agcggatatt aactatacat caggcttcag aaattcagac    660
cggattcttt actcaagcga ctggctgatt acaaaacaa cggaccatta tcagaccttt    720
acaaaaatca gataacgaaa aaacggctt ccctgcggag gccgtttttt tcagctttac    780
ataaagtgtg taataaattt ttcttcaaac tctgatcggt caatttcact tt           832

<210> SEQ ID NO 16
<211> LENGTH: 4733
<212> TYPE: DNA
<213> ORGANISM: Artificial Sequence
<220> FEATURE:
<223> OTHER INFORMATION: GFP gene from cloning vector

<400> SEQUENCE: 16
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atctcgagct caagcttcga attctgcagt cgacggtacc gcgggcccgg    660
gatccaccgt cgccaccat ggtgagcaag ggcgaggagc tgttcaccgg ggtggtgccc    720
atcctggtcg agctggacgg cgacgtaaac ggccacaagt tcagcgtgtc cggcgagggc    780
gagggcgatg ccacctacgg caagctgacc ctgaagttca tctgcaccac cggcaagctg    840
cccgtgccct ggcccaccct cgtgaccacc ctgacctacg gcgtgcagtg cttcagccgc    900
taccccgacc acatgaagca gcacgacttc ttcaagtccg ccatgcccga aggctacgtc    960
caggagcgca ccatcttctt caaggacgac ggcaactaca agacccgcgc cgaggtgaag   1020
ttcgagggcg acaccctggt gaaccgcatc gagctgaagg gcatcgactt caaggaggac   1080
ggcaacatcc tggggcacaa gctggagtac aactacaaca gccacaacgt ctatatcatg   1140
gccgacaagc agaagaacgg catcaaggtg aacttcaaga tccgccacaa catcgaggac   1200
ggcagcgtgc agctcgccga ccactaccag cagaacaccc ccatcggcga cggccccgtg   1260
ctgctgcccg acaaccacta cctgagcacc cagtccgccc tgagcaaaga ccccaacgag   1320
aagcgcgatc acatggtcct gctggagttc gtgaccgccg ccgggatcac tctcggcatg   1380
gacgagctgt acaagtaaag cggccgcgac tctagatcat aatcagccat accacatttg   1440
tagaggtttt acttgcttta aaaaacctcc cacacctccc cctgaacctg aaacataaaa   1500
tgaatgcaat tgttgttgtt aacttgttta ttgcagctta atggttac aaataaagca    1560 atagcatcac aaatttcaca aataaagcat ttttttcact gcattctagt tgtggtttgt   1620
ccaaactcat caatgtatct taaggcgtaa attgtaagcg ttaatatttt gttaaaattc   1680
gcgttaaatt tttgttaaat cagctcattt tttaaccaat aggccgaaat cggcaaaatc   1740
ccttataaat caaagaata gaccgagata ggggttgagtg ttgttccagt ttggaacaag   1800
agtccactat taaagaacgt ggactccaac gtcaaagggc gaaaaaccgt ctatcagggc   1860
```

```
gatggcccac tacgtgaacc atcaccctaa tcaagttttt tggggtcgag gtgccgtaaa   1920
gcactaaatc ggaaccctaa agggagcccc cgatttagag cttgacgggg aaagccggcg   1980
aacgtggcga gaaggaagg gaagaaagcg aaaggagcgg gcgctagggc gctggcaagt    2040
gtagcggtca cgctgcgcgt aaccaccaca cccgccgcgc ttaatgcgcc gctacagggc   2100
gcgtcaggtg gcacttttcg gggaaatgtg cgcggaaccc ctatttgttt attttctaa    2160
atacattcaa atatgtatcc gctcatgaga caataaccct gataaatgct tcaataatat   2220
tgaaaagga agagtcctga ggcggaaaga accagctgtg gaatgtgtgt cagttagggt    2280
gtggaaagtc cccaggctcc ccagcaggca gaagtatgca aagcatgcat ctcaattagt   2340
cagcaaccag gtgtggaaag tccccaggct ccccagcagg cagaagtatg caaagcatgc   2400
atctcaatta gtcagcaacc atagtcccgc ccctaactcc gcccatcccg cccctaactc   2460
cgcccagttc cgcccattct ccgccccatg gctgactaat ttttttttatt tatgcagagg   2520
ccgaggccgc ctcggcctct gagctattcc agaagtagtg aggaggcttt tttggaggcc   2580
taggcttttg caaagatcga tcaagagaca ggatgaggat cgtttcgcat gattgaacaa   2640
gatggattgc acgcaggttc tccggccgct tgggtggaga ggctattcgg ctatgactgg   2700
gcacaacaga caatcggctg ctctgatgcc gccgtgttcc ggctgtcagc gcaggggcgc   2760
ccggttcttt ttgtcaagac cgacctgtcc ggtgccctga atgaactgca agacgaggca   2820
gcgcggctat cgtggctggc cacgacgggc gttccttgcg cagctgtgct cgacgttgtc   2880
actgaagcgg gaagggactg gctgctattg ggcgaagtgc cggggcagga tctcctgtca   2940
tctcaccttg ctcctgccga gaaagtatcc atcatggctg atgcaatgcg gcggctgcat   3000
acgcttgatc cggctacctg cccattcgac caccaagcga aacatcgcat cgagcgagca   3060
cgtactcgga tggaagccgg tcttgtcgat caggatgatc tggacgaaga gcatcagggg   3120
ctcgcgccag ccgaactgtt cgccaggctc aaggcgagca tgcccgacgg cgaggatctc   3180
gtcgtgaccc atggcgatgc ctgcttgccg aatatcatgg tggaaaatgg ccgcttttct   3240
ggattcatcg actgtggccg gctgggtgtg gcggaccgct atcaggacat agcgttggct   3300
acccgtgata ttgctgaaga gcttggcggc gaatgggctg accgcttcct cgtgctttac   3360
ggtatcgccg ctcccgattc gcagcgcatc gccttctatc gccttcttga cgagttcttc   3420
tgagcgggac tctggggttc gaaatgaccg accaagcgac gcccaacctg ccatcacgag   3480
atttcgattc caccgccgcc ttctatgaaa ggttgggctt cggaatcgtt ttccgggacg   3540
ccggctggat gatcctccag cgcggggatc tcatgctgga gttcttcgcc cacccctaggg  3600
ggaggctaac tgaaacacgg aaggagacaa taccggaagg aacccgcgct atgacggcaa   3660
taaaagaca gaataaaacg cacggtgttg ggtcgtttgt tcataaacgc ggggttcggt   3720
cccagggctg gcactctgtc gataccccac cgagacccca ttggggccaa tacgcccgcg   3780
tttcttcctt ttccccaccc cacccccaa gttcgggtga aggcccaggg ctcgcagcca   3840
acgtcggggc ggcaggccct gccatagcct caggttactc atatatactt tagattgatt   3900
taaaacttca ttttttaattt aaaaggatct aggtgaagat cctttttgat aatctcatga   3960
ccaaaatccc ttaacgtgag ttttcgttcc actgagcgtc agacccgta gaaaagatca   4020
aaggatcttc ttgagatcct ttttttctgc gcgtaatctg ctgcttgcaa acaaaaaaac   4080
caccgctacc agcggtggtt tgtttgccgg atcaagagct accaactctt tttccgaagg   4140
taactggctt cagcagagcg cagataccaa atactgtcct tctagtgtag ccgtagttag   4200
```

```
gccaccactt caagaactct gtagcaccgc ctacatacct cgctctgcta atcctgttac    4260
cagtggctgc tgccagtggc gataagtcgt gtcttaccgg gttggactca agacgatagt    4320
taccggataa ggcgcagcgg tcgggctgaa cggggggttc gtgcacacag cccagcttgg    4380
agcgaacgac ctacaccgaa ctgagatacc tacagcgtga gctatgagaa agcgccacgc    4440
ttcccgaagg gagaaaggcg gacaggtatc cggtaagcgg cagggtcgga acaggagagc    4500
gcacgaggga gcttccaggg ggaaacgcct ggtatcttta tagtcctgtc gggtttcgcc    4560
acctctgact tgagcgtcga ttttttgtgat gctcgtcagg ggggcggagc ctatggaaaa    4620
acgccagcaa cgcggccttt ttacggttcc tggccttttg ctggccttttt gctcacatgt    4680 tctttcctgc gttatcccct gattctgtgg ataaccgtat taccgccatg cat           4733
```

```
<210> SEQ ID NO 17
<211> LENGTH: 45
<212> TYPE: DNA
<213> ORGANISM: Artificial Sequence
<220> FEATURE:
<223> OTHER INFORMATION: barnase coding sequence with SV40LT intron

<400> SEQUENCE: 17
ccccgaattc gccaccatgg cacaggtatt tgcttcttcc ttaaa                     45

<210> SEQ ID NO 18
<211> LENGTH: 30
<212> TYPE: DNA
<213> ORGANISM: Artificial Sequence
<220> FEATURE:
<223> OTHER INFORMATION: barnase coding sequence with SV40LT

<400> SEQUENCE: 18
tgttgataac ctaaaataca caaacaatta                                       30

<210> SEQ ID NO 19
<211> LENGTH: 30
<212> TYPE: DNA
<213> ORGANISM: Artificial Sequence
<220> FEATURE:
<223> OTHER INFORMATION: the barnase coding sequence together with GFP
      coding sequence

<400> SEQUENCE: 19
tgtattttag gttatcaaca cgtttgacgg                                       30

<210> SEQ ID NO 20
<211> LENGTH: 32
<212> TYPE: DNA
<213> ORGANISM: Artificial Sequence
<220> FEATURE:
<223> OTHER INFORMATION: barnase coding sequence together with GFP
      coding sequence

<400> SEQUENCE: 20 gggggggtacc tcattacttg tacagctcgt cc                                   32

<210> SEQ ID NO 21
<211> LENGTH: 45
<212> TYPE: DNA
<213> ORGANISM: Artificial Sequence
<220> FEATURE:
<223> OTHER INFORMATION: barnase coding sequence with GFP and CMV

<400> SEQUENCE: 21
ccccgaattc gccaccatgg cacaggtatt tgcttcttcc ttaaa                     45
```

<210> SEQ ID NO 22
<211> LENGTH: 32
<212> TYPE: DNA
<213> ORGANISM: Artificial Sequence
<220> FEATURE:
<223> OTHER INFORMATION: barnase coding sequence with GFP and CMV

<400> SEQUENCE: 22 gggggtacc tcattacttg tacagctcgt cc            32

<210> SEQ ID NO 23
<211> LENGTH: 30
<212> TYPE: DNA
<213> ORGANISM: Homo sapiens

<400> SEQUENCE: 23
gcgcacgcgt atcatcagct tttcaaagac              30

<210> SEQ ID NO 24
<211> LENGTH: 30
<212> TYPE: DNA
<213> ORGANISM: Homo sapiens

<400> SEQUENCE: 24
cgcgaccggt cgctgcctga aactcgcgcc              30

<210> SEQ ID NO 25
<211> LENGTH: 24
<212> TYPE: DNA
<213> ORGANISM: Artificial Sequence
<220> FEATURE:
<223> OTHER INFORMATION: baculovirus gp64 gene

<400> SEQUENCE: 25
ccctctgtgt acttggctct aacg                    24

<210> SEQ ID NO 26
<211> LENGTH: 25
<212> TYPE: DNA
<213> ORGANISM: Artificial Sequence
<220> FEATURE:
<223> OTHER INFORMATION: baculovirus gp64 gene

<400> SEQUENCE: 26
cggtgaaacg caaagtcgag caccg                   25

<210> SEQ ID NO 27
<211> LENGTH: 35
<212> TYPE: DNA
<213> ORGANISM: Homo sapiens

<400> SEQUENCE: 27
ccgcacgcgt cttagaaata tgggggtagg ggtgg         35

<210> SEQ ID NO 28
<211> LENGTH: 33
<212> TYPE: DNA
<213> ORGANISM: Homo sapiens

<400> SEQUENCE: 28
ctcaaactct agtggcctgg ataaagctga gtg            33

<210> SEQ ID NO 29

```
<211> LENGTH: 37
<212> TYPE: DNA
<213> ORGANISM: Homo sapiens

<400> SEQUENCE: 29
ctttatccag gccactagag tttgaggaga atatttg                              37

<210> SEQ ID NO 30
<211> LENGTH: 33
<212> TYPE: DNA
<213> ORGANISM: Homo sapiens

<400> SEQUENCE: 30
acttacctga ccggttgcta gttattttgt tat                                  33

<210> SEQ ID NO 31
<211> LENGTH: 34
<212> TYPE: DNA
<213> ORGANISM: Homo sapiens

<400> SEQUENCE: 31
ggggactagt ctggccatag aaccagagaa gtga                                 34

<210> SEQ ID NO 32
<211> LENGTH: 34
<212> TYPE: DNA
<213> ORGANISM: Homo sapiens

<400> SEQUENCE: 32
ttttaccggt ccacctctgc caacgggtcc cgcg                                 34

<210> SEQ ID NO 33
<211> LENGTH: 30
<212> TYPE: DNA
<213> ORGANISM: Homo sapiens

<400> SEQUENCE: 33
gcccactagt tgaggtacct ggtgtagttt                                      30

<210> SEQ ID NO 34
<211> LENGTH: 30
<212> TYPE: DNA
<213> ORGANISM: Homo sapiens

<400> SEQUENCE: 34
atataccggt cagcggcggg cagggcgcgg                                      30

<210> SEQ ID NO 35
<211> LENGTH: 33
<212> TYPE: DNA
<213> ORGANISM: Homo sapiens

<400> SEQUENCE: 35
gcccactagt acccaggtac ctatgttcaa aag                                  33

<210> SEQ ID NO 36
<211> LENGTH: 32
<212> TYPE: DNA
<213> ORGANISM: Homo sapiens

<400> SEQUENCE: 36
gcgcaccggt ttgcctgctg ctttccacca ag                                   32
```

```
<210> SEQ ID NO 37
<211> LENGTH: 30
<212> TYPE: DNA
<213> ORGANISM: Homo sapiens

<400> SEQUENCE: 37
gcccactagt taccgaccac ccgcaaacag                              30

<210> SEQ ID NO 38
<211> LENGTH: 30
<212> TYPE: DNA
<213> ORGANISM: Homo sapiens

<400> SEQUENCE: 38
gcgcaccggt gtaaccgctg gttctccaga                              30

<210> SEQ ID NO 39
<211> LENGTH: 844
<212> TYPE: DNA
<213> ORGANISM: Artificial Sequence
<220> FEATURE:
<223> OTHER INFORMATION: DT-A coding sequence comprising the hGH intron

<400> SEQUENCE: 39
atgggcgctg atgatgttgt tgattcttct aaatcttttg tgatggaaaa cttttcttcg      60
taccacggga ctaaacctgg ttatgtagat tccattcaaa aaggtaagcg cccctaaaat     120 cccttttggca caatgtgtcc tgaggggaga ggcagcgacc tgtagatggg acggggggcac   180 taaccctcag ggtttggggt tctgaatgtg agtatcgcca tgtaagccca gtatttggcc     240
aatctcagaa agctcctggc tccctggagg atggagagag aaaaacaaac agctcctgga    300
gcagggagag tgctggcctc ttgctctccg gctccctctg ttgccctctg gtttctcccc     360
aggtatacaa aagccaaaat ctggtacaca aggaaattat gacgatgatt ggaaagggtt     420
ttatagtacc gacaataaat acgacgctgc gggatactct gtagataatg aaaacccgct     480
ctctggaaaa gctggaggcg tggtcaaagt gacgtatcca ggactgacga aggttctcgc     540
actaaaagtg gataatgccg aaactattaa gaaagagtta ggtttaagtc tcactgaacc     600
gttgatggag caagtcggaa cggaagagtt tatcaaaagg ttcggtgatg gtgcttcgcg     660
tgtagtgctc agccttccct tcgctgaggg gagttctagc gttgaatata ttaataactg     720
ggaacaggcg aaagcgttaa gcgtagaact tgagattaat tttgaaaccc gtggaaaacg     780
tggccaagat gcgatgtatg agtatatggc tcaagcctgt gcaggaaatc gtgtcaggcg     840
atga                                                                  844

<210> SEQ ID NO 40
<211> LENGTH: 694
<212> TYPE: DNA
<213> ORGANISM: Artificial Sequence
<220> FEATURE:
<223> OTHER INFORMATION: DT-A coding sequence comprising the SV40LT
      antigen intron

<400> SEQUENCE: 40
atggcacagg tatttgcttc ttccttaaat cctggtgttg atgcaatgta ctgcaaacaa      60
tggcctgagt gtgcaaagaa aatgtctgct aactgcatat gcttgctgtg cttactgagg     120
atgaagcatg aaaatagaaa attatacagg aaagatccac ttgtgtgggt tgattgctac    180
tgcttcgatt gctttagaat gtggtttgga cttgatcttt gtgaaggaac cttacttctg     240
tggtgtgaca taattggaca aactacctac agagatttaa agctctaagg taaatataaa     300
```

-continued

```
atttttaagt gtataatgtg ttaaactact gattctaatt gtttgtgtat tttaggttat    360
caacacgttt gacggggttg cggattatct tcagacatat cataagctac ctgataatta    420
cattacaaaa tcagaagcac aagccctcgg ctgggtggca tcaaaaggga accttgcaga    480
cgtcgctccg ggaaaagca tcggcggaga catcttctca aacagggaag gcaaactcca     540
gggcaaaagc ggacgaacat ggcgtgaagc ggatattaac tatacatcag gcttcagaaa    600
ttcagaccgg attctttact caagcgactg gctgatttac aaaacaacgg accattatca    660
gacctttaca aaaatcagaa tggtgagcaa gggc                                694

<210> SEQ ID NO 41
<211> LENGTH: 15
<212> TYPE: DNA
<213> ORGANISM: Artificial Sequence
<220> FEATURE:
<223> OTHER INFORMATION: GFP sequence with DT-A coding sequence
      comprising the SV40LT antigen intron

<400> SEQUENCE: 41
gagctgtaca agtaa                                                      15
```

VECTORS HARBORING TOXIC GENES, METHODS AND USES THEREFOR

RELATED APPLICATIONS

This application is a National Stage entry application of and claims the benefit of PCT/US12/60441 international filing date 16 Oct. 2012 and claims the benefit of U.S. Provisional Patent Application 61/568,595 filed 8 Dec. 2011 and U.S. Provisional Patent Application 61/618,689 filed 31 Mar. 2012. These applications are incorporated by reference, each in its entirety.

INCORPORATION BY REFERENCE OF SEQUENCE LISTING

The Sequence Listing, which is a part of the present disclosure, includes a computer readable form and a written sequence listing comprising nucleotide and/or amino acid sequences. The sequence listing information recorded in computer readable form is identical to the written sequence listing. The subject matter of the Sequence Listing is incorporated herein by reference in its entirety.

INTRODUCTION

The present disclosure is in the field of virology, and, more particularly, in the field of nucleic acid vectors that can be grown in insect cells and used for treatment of mammalian diseases such as cancer.

Toxic genes and proteins encoded by such genes have been used or proposed for use for disease therapies involving inducing cell death, such as, for example cancer therapies involving expression of genes that cause cell death. Suicide gene therapy has become an attractive strategy for cancer treatment (See, e.g., Rodriguez, R. and Simons, J. W. Urology 54: 401-406, 1999). Suicide gene therapy relies on the delivery of genes whose products are toxic, or which produce a toxic product in conjunction with pro-drug administration (Denning, C., et al., Human Gene Therapy 8: 1825-1835, 1997). Suicide gene therapy has been widely investigated for the treatment of human immunodeficiency virus (HIV) infection, for controlling graft-versus-host disease, and also for the treatment of cancer. The generation of viral vectors containing toxin genes such as diphtheria toxin A fragment (DT-A), Pseudomonas exotoxin (PE) or barnase has been difficult to fulfill due to the extreme toxicity of these toxins.

Certain proteins encoded by toxic genes can kill a host cell at very low levels of expression. For example, a single molecule of diphtheria toxin (DT-A) can kill a cell (Yamaizumi, M. et al. (1978) Cell 15: 245-250). DT is believed to poison protein synthesis by catalyzing ADP-ribosylation of elongation factor 2 (EF2). DT kills primarily by an apoptosis-mediated pathway, and is believed to kill cells in a cell-cycle independent fashion. This makes DT an attractive cancer therapeutic, as some malignancies such as prostate cancer tend to have a very low mitotic index. Similarly, the ribonuclease barnase has been suggested as a potent toxic agent for targeting to cancer cells (Edelweiss, E., et al., PLoS ONE 3: e2434, 2008).

However, production of viral vectors, such as recombinant adenovirus, recombinant baculovirus, and adeno-associated virus which could be used for delivery of toxic genes to a target cell such as a cancer cell, can be hampered by the toxicity of a toxic gene to the host cell. A viral vector harboring a toxic gene thus must not only be grown under conditions that are not lethal to a host cell that is used for growing the vector, but the vector also must be able to effect toxicity upon a target cell such as a cancer cell.

Previous attempts at limiting toxicity of a toxic gene such as DT-A by use of an inducible and/or tissue specific promoter have led to variable results. For example, Maxwell et al. (Cancer Res. 46:4660-4664, 1986) used a truncated form of the metallothionein promoter to demonstrate that basal expression of this promoter, even in the absence of heavy metals, resulted in substantial inhibition of protein synthesis. This inhibition could be augmented by the addition of an immunoglobulin enhancer element but only minimally by cadmium. The authors were not able to demonstrate true specific cytotoxicity but rather only a preferential cell susceptibility to DT-A-mediated cell death, presumably as a result of basal expression of this highly toxic gene. This group also introduced an attenuated mutant of DT-A (Maxwell, F. et al. (1987) Mol. Cell. Biol. 7:1576-1579) (Robinson, D. F. and Maxwell, I. H. (1995) Hum. Gene Ther. 6:137-143. Subsequent efforts by this group and others concentrated on introducing an attenuated mutant of DT-A (Maxwell, F. et al. (1987) Mol. Cell. Biol. 7:1576-1579) or on tightly regulating gene expression using prokaryotic control elements (Robinson, D. F. and Maxwell, I. H. (1995) Hum. Gene Ther. 6:137-143; Paulus, W. et al. (1997) J. Neurosurg. 87:89-95). In both cases, although preferential cell killing could be demonstrated, complete abolition of nonspecific cell killing was not achieved. Keyvani et al. (Life Sci. 64:1719-1724, 1999) used a tet repressor-based system for expressing an attenuated DT-A mutant, but these workers concluded that (1) expression but not toxicity of the DT-A mutant can be sufficiently controlled by a tetracycline-responsive promoter.

U.S. Pat. No. 7,582,290 to Rodriguez, R., et al. discloses replication-deficient Adenovirus (Ad) expressing the A subunit of diphtheria toxin (DT-A) driven by prostate-specific promoters for use in suicide gene therapy for prostate cancer. This patent describes a mutation of glycine to arginine in position 705 of the EF-2 protein that gives resistance to inhibition of protein synthesis by DT. The inventors in this patent assert that a major problem in the application of replication-defective adenovirus in gene therapy is the presence of replication-competent adenovirus (RCA), which is generated by recombination between sequences in the Ad vector and homologous Ad sequences in the helper cells. These inventors also disclose a DT-resistant helper cell line, DPL, for packaging DT-expressing adenovirus for suicide gene therapy, in which the cells do not make RCA. These inventors further disclose that they amplified a 500 bp region from the EF-2 gene spanning the codon 705, from TSU cells (a prostate cancer cell line). Using site directed mutagenesis, these inventors changed codon 705 from "GGA" to "AGA" to code for arginine instead of glycine. Using homologous recombination they replaced glycine with arginine in position 705 of the EF-2 protein in PER.C6 cells (derived from diploid human embryonic retinoblasts ("HER") and described in U.S. Pat. Nos. 5,994,128, 6,265,212, 6,033,908, and 6,306, 652), and generated a DT-resistant helper cell line for packaging adenoviral vectors. These cells contain the Ad serotype 5 (Ad5) E1-A & E1-B encoding sequences (Ad5 neucleotides 459-3510) under the control of human phosphoglycerate kinase (PGK) promoter. According to these inventors, these cells, used in conjunction with non-overlapping E1-deleted adenovirus, eliminates the presence of RCA in viral preps.

Wang et al., (Wang, C-Y, et al., Cancer Research 66: 5798-5806, 2006) described a recombinant baculovirus accommodating the transcriptional regulatory sequence of glial fibrillary acidic acid protein (GFAP) to drive the expression of DT-A gene in glioma cells. Because GFAP promoter is inactive in insect cells, they were able to generate recombinant baculovirus carrying the DT-A toxic gene. However, a cell-type specific promoter such as GFAP promoter displays relatively weak transcriptional activity compared to positive control sequences derived from viruses, e.g. the enhancer/promoter of human cytomegalovirus (CMV) immediate-early gene and therefore limits its applications.

Kohlschütter, et al., Toxins 2: 2754-2768, 2010 described AAV vectors carrying the DT-A gene, in which the Tet$^R$ repressor system was used to decrease the expression of DT-A. Even though the authors produced some AAV vectors carrying the DT-A gene in HEK293T cells, their AAV yields were generally 2 to 3 logs lower than AAV vectors that did not carry the DT-A gene, such as vectors carrying the PUMA gene (AAVTetO2-PUMA). The authors attributed the lower titer to residual expression of the DTA protein.

U.S. Pat. No. 6,723,551 to Kotin et al. describes methods of production of adeno-associated virus (AAV) in insect cells. These inventors assert that introns comprised by AAV genes are not properly spliced in insect cells. These inventors produced AAV in insect cells by using AAV genes engineered to be devoid of introns. However, this patent neither teaches nor suggests growing vectors harboring toxic genes in insect cells.

There currently exists a need for additional compositions and methods for producing suicide gene therapy vectors for therapeutic use such as use in killing cancer cells.

SUMMARY

In view of a need to grow viral vectors harboring toxic genes in insect cells, the present inventor has developed modified baculoviral and adeno-associated viral vectors comprising toxic genes, insect cells comprising such vectors, methods of making such vectors and cells, and methods of treatment that use such vectors.

A nucleic acid of the present teachings can be a nucleic acid for growing a toxic gene in an insect cell. In some configurations, a nucleic acid can comprise, consist essentially of, or consist of a sequence encoding a toxic polypeptide, and an intron that interrupts the sequence, whereby an RNA comprising the intron can be spliced by mammalian cells but not by insect cells, to form in mammalian cells, but not in insect cells, a translatable mRNA that, upon translation, yields cell-toxic levels of a toxic polypeptide. In some configurations, a nucleic acid can comprise a sequence encoding a toxic polypeptide such as, without limitation, diphtheria toxin (DT-A), barnase, ricin, abrin, Pseudomonas exotoxin or a pro-apoptotic polypeptide. Sequences encoding such toxic polypeptides (and peptides) are well known to skilled artisans (see, e.g., Ellerby, H. M., et al., Nature Medicine 5: 1032-1038, 1999) and are available from publically accessible resources such as, for example, the website of the National Center for Biotechnology Information. In some configurations, the nucleic acid can encode a toxic polypeptide such as a diphtheria toxin, for example DT-A. In some configurations, the nucleic acid can encode a toxic polypeptide such as barnase.

In various configurations, an intron of the present teachings can be any intron which is not properly spliced out in insect cells but is properly spliced by mammalian cells, such as, for example and without limitation, an intron from a human growth hormone gene or an intron from a SV40 large T antigen gene.

In various configurations, a nucleic acid of the present teachings can further comprise an expression control sequence operably linked to the sequence encoding a toxic polypeptide. An expression control sequence can be, for example, a promoter, an IRES, an enhancer and/or a combination thereof.

In non-limiting illustration, FIG. 1 presents genetic and transcriptional maps of a toxic gene such as a DT-A gene comprising an intron and operably linked to a promoter such as a CMV promoter. Upon introduction of a DT-A gene comprising an intron of the present teachings into a mammalian cell, the gene is transcribed, and mature DT-A mRNA is formed in the mammalian cell through intron splicing. The mature RNA is translated into functional DT-A protein to kill the cell. The numbers above the genetic map based on DT-A coding sequence (Genbank access no. X00703) indicate the nucleotide positions where the intron is inserted. CMVpr=cytomegalovirus promoter; DT-A=Diptheria Toxin A nucleic acid sequence; pA=polyadenylation signal.

In some embodiments, the present teachings include a viral vector comprising a nucleic acid as described supra. In various configurations, a viral vector can be, for example, a baculovirus, a retrovirus, an adenovirus, an adeno-associated virus (AAV) or a combination thereof, such as, for example, a baculovirus comprising AAV sequences, such as described, for example, in US Patent Application Publication 20090203071 but modified to also include sequences encoding a toxic gene in which the coding sequence is disrupted with an intron.

In some embodiments, the present teachings include an insect cell in vitro which comprises a nucleic acid described supra, or a viral genome comprising the nucleic acid as described supra.

In various configurations, an insect cell can be, without limitation, a cell of an established insect cell line known to skilled artisans, such as, without limitation, a *Trichoplusia ni* BTI-Tn-5B1-4 cell, a *Spodoptera frugiperda* Sf9 cell or a *Spodoptera frugiperda* Sf21 cell.

In some embodiments, the present teachings include a cell culture comprising a plurality of cells described supra; and a culture medium. In various configurations, such cell lines can accumulate a virus such as, for example, AAV, wherein unconcentrated cell culture medium can comprise the virus at a titer greater than $10^9$ AAV genomes/ml, greater than $10^{10}$ AAV genomes/ml, greater than $10^{11}$ AAV genomes/ml, or greater than $10^{12}$ AAV genomes/ml. For example, in various configurations, 1 liter of unconcentrated cultured cell medium can comprise at least $10^{13}$, at least $10^{14}$, or at least $10^{15}$ AAV viral particles within 3 days after infection of an insect cell culture with a baculovirus of the present teachings.

In various configurations, a cell line or cell culture of the present teachings can accumulate a baculovirus, wherein unconcentrated cell culture medium can comprise the virus at a titer greater than $10^9$ pfu/l, greater than $10^{10}$ pfu/l, greater than $10^{11}$ pfu/l, or greater than $10^{12}$ pfu/l within 4 days following transfection.

In some embodiments, the present teachings include methods of growing a vector comprising a toxic gene in vitro. In various configurations, these methods include: providing a cell culture comprising insect cells; infecting or transfecting the cells with a nucleic acid or a virus of the present teachings; and incubating the cells under conditions suitable for virus production.

In some embodiments, the present teachings include methods of treating a cancer. In various configurations, these methods include administering a nucleic acid or a virus of the present teachings to a subject in need of therapy. In some configurations, the virus can be a baculovirus or an adeno-associated virus. A cancer subject to treatment using a nucleic acid or a virus of the present teachings can be any cancer, such as, without limitation, a prostate cancer, a breast cancer, a brain tumor, a cervical cancer or a nasopharyngeal carcinoma. In various embodiments of the present teachings, a virus of the present teachings, such as an AAV of the present teachings or a baculovirus of the present teachings, can be a virus that can infect a mammalian cell but cannot replicate within the mammalian cell.

In various embodiments, the present teachings include use of a nucleic acid or virus described supra for the treatment of a disease such as, for example, cancer.

In various embodiments, the present teachings include a nucleic acid or virus described herein for use in the treatment of a cancer. In various embodiments, the present teachings include a nucleic acid or virus described herein for use in the manufacture of a medicament for the treatment of a cancer.

In various embodiments, the present teachings include a recombinant baculovirus or nucleic acid comprising a toxic gene (such as, without limitation, a DT-A gene or a barnase gene) which further comprises an intron, such that a mammalian cell but not in an insect cell can express a mature mRNA that can be translated by the host cell to produce a polypeptide that is lethal to the host cell. In some configurations, an intron that disrupts coding sequence of a toxic gene can be spliced from a transcript of the toxic gene by a mammalian cell, but not by an insect cell, for example as set forth in FIG. 1. Upon introduction of a toxic gene comprising an intron into a mammalian cell (such as a human cell in vitro or in vivo), the cell can produce mature mRNA of the toxic gene. The mature mRNA can be translated by the mammalian cell into functional DT-A protein (or other toxic protein) to kill the cell.

In some embodiments, the present teachings include methods of producing recombinant baculovirus carrying a toxic gene comprising an intron in insect cells. In these embodiments, recombinant baculovirus can be generated according to methods well known to skilled artisans. Without limitation, such methods can include, for example, transfecting Bacmid DNA's into insect cells in vitro, such as Sf9 cells, with a vector such as a Bacmid modified to comprise a toxic gene into which an intron is inserted.

Some embodiments of the present teachings include AAV vectors carrying a toxic gene such as a DT-A gene comprising an intron or a barnase gene comprising an intron. AAV vectors comprising a toxic gene with an intron can be produced in insect cells. Upon introduction into a host mammalian cell, a toxic gene comprised by an AAV vector of the present teachings can be transcribed and spliced in the mammalian cell to form a mature toxic gene mRNA (such as a DT-A mRNA or a barnase mRNA). A mature toxic gene mRNA can be translated by the host mammalian cell to yield a toxic protein (such as DT-A or barnase), thereby disabling or killing the host mammalian cell.

Some embodiments of the present teachings include methods of producing AAV vectors carrying a toxic gene such as, for example, a DT-A gene or barnase gene in insect cells. In these methods, a first vector comprising baculovirus and AAV sequences, such as, for example, Bac-Rep-Cap (or Bac-in-Cap-inRep), and a second vector comprising baculovirus and ITR sequences as well as a toxic gene (such as, for example, DT-A or barnase) interrupted by an intron, can be contacted with a host insect cell to co-infect the host cell. An infected cell can yield AAV comprising the toxic gene interrupted by an intron. Such infected cells grown in vitro can yield titers of recombinant AAV comprising a toxic gene, of at least $10^9$ viral genomes/ml, at least $10^{10}$ viral genomes/ml, at least $10^{11}$ viral genomes/ml, or at least $10^{12}$ viral genomes/ml in unconcentrated culture medium within 3 days after infection of a culture of insect cells such as Sf9 cells.

Some embodiments of the present teachings include additional methods of producing AAV vectors carrying a toxic gene in insect cells. In these methods, an insect cell can be provided comprising a stably integrated transgene such as a transgene comprising AAV ITRs flanking a toxic gene (such as DT-A or barnase) comprising an intron. See, e.g., FIG. 5. A cell of these embodiments can be infected with Bac-Rep-Cap. Following infection with Bac-Rep-Cap, the cell can produce AAV vectors comprising a toxic gene (such as DT-A) comprising an intron. In various configurations, a population of infected cells grown in vitro can yield titers of recombinant AAV, of at least $10^9$ viral genomes/ml, at least $10^{10}$ viral genomes/ml, at least $10^{11}$ viral genomes/ml, or at least $10^{12}$ viral genomes/ml in unconcentrated culture medium. In some configurations, such high can be obtained within about 3 days after infection.

In some embodiments, the present teachings include production of AAV vectors carrying toxic genes using insect cells (such as, for example, Sf9 cell) harboring stably integrated AAV genomes carrying inDTA or inBarnase. In various configurations, such cells can be infected with recombinant baculovirus carrying Rep and Cap genes for 3 days. The cell pellets can be harvested and processed to purify the AAV vectors.

Accordingly, in some embodiments, the present teachings include nucleic acids comprising a sequence encoding a toxic polypeptide, and an intron that interrupts the sequence, whereby the intron is spliced in mammalian cells but not in insect cells to form an mRNA that is translated to form cell-toxic levels of the toxic polypeptide in mammalian cells but not in insect cells. In some configurations, the toxin polypeptide encoded by a toxin gene can be, without limitation, diphtheria toxin (DT-A), barnase, ricin, abrin, or Pseudomonas exotoxin. In some preferred configurations, the toxin can be diphtheria toxin (DT-A) or barnase, encoded by a diphtheria toxin (DT-A) gene or a barnase gene, respectively, but interrupted by an intron such as, without limitation, a human growth hormone intron or an SV40 large T-antigen intron. In various configurations, a nucleic acid of the present teachings can further comprise at least one expression element operably linked to the sequence. Such expression elements can include one or more of a promoter, an IRES, an enhancer and a combination thereof. In some configurations, expression elements comprised by a nucleic acid of the present teachings can include one or more of a CMV promoter, an AFP promoter, an AFP enhancer, a SURV promoter, a CXCR4 promoter, a TERT promoter, a COX2 promoter, and a CCKAR promoter. In some configurations, expression elements comprised by a nucleic acid of the present teachings can include one or more of a hAFP promoter, a hAFP enhancer, an hSURV promoter, a hCXCR4 promoter, an hTERT promoter, a hCOX2 promoter, and a hCCKAR promoter. In some configurations, an expression control element can be a promoter that can direct expression in tumor cells, such as an hSURV promoter or a CXCR4 promoter. In some preferred configurations, an expression element can be an hSURV or a CXCR4 promoter.

In some embodiments, an intron that disrupts the sequence of a toxic gene can be any intron that is spliced by mammalian cells but not insect cells. In various configurations, the intron can be an artificial intron, a human growth hormone intron, or an SV40 large T-antigen intron.

In various embodiments, a nucleic acid or viral vector of the present teachings can comprise at least one ITR.

In some embodiments, a nucleic acid or viral vector of the present teachings can comprise, in 5' to 3' order, a first ITR, a promoter, a first portion of a toxic gene, an intron, a second portion of the toxic gene, a polyadenylation signal, and a second ITR. In various configurations, the first ITR can be an AAV ITR, and the second ITR can be an AAV ITR.

Some embodiments of the present teachings include viral vectors comprising the nucleic acids described herein. In some configurations, a viral vector can be, without limitation, a baculovirus, a retrovirus, an adenovirus, an adeno-associated virus (AAV) or a combination thereof, and in particular a vector can be a baculovirus, an adeno-associated virus (AAV), or a combination thereof. Non-limiting examples of AAV comprising a nucleic acid of the present teachings include AAV2 and AAV9, preferably AAV2.

Some embodiments of the present teachings include insect cells in vitro comprising the nucleic acids described herein. Various embodiments of the present teachings include individual insect cells in vitro, insect cell lines, insect cell cultures, and insect cell populations in vitro. In various configurations, an insect cell of the present teachings can include, without limitation, a Trichoplusia ni BTI-Tn-5B1-4 cell, a Spodoptera frugiperda Sf9 cell or a Spodoptera frugiperda Sf21 cell; an insect cell population or cell culture can include, without limitation, Trichoplusia ni BTI-Tn-5B1-4 cells, Spodoptera frugiperda Sf9 cells, Spodoptera frugiperda Sf21 cells, and any combination thereof. In various configurations, an insect cell can comprise a nucleic acid which is comprised by a viral genome. In some embodiments, an insect cell of the present teachings can comprise a virus which comprises a nucleic acid of the present teachings. In various configurations, a virus of these embodiments can be an AAV, a baculovirus, or a combination thereof. In some embodiments, an insect cell of the present teachings can be stably transformed with a nucleic acid of the present teachings.

Embodiments of the present teachings include cell cultures such as insect cell cultures. In various configurations, a cell culture can include cells comprising a nucleic acid of the present teachings, and a cell culture medium. In various configurations, a cell culture can comprise greater than $10^9$ viral genomes/ml without concentration of the cell culture medium, greater than $10^{10}$ viral genomes/ml without concentration of the cell culture medium, greater than $10^{11}$ viral genomes/ml without concentration of the cell culture medium, greater than $10^{12}$ viral genomes/ml without concentration of the cell culture medium. In various embodiments, a cell line, cell culture or cell population of the present teachings can comprise a baculovirus comprising a nucleic acid of the present teachings. In various configurations, a cell line, cell culture or cell population can comprise baculovirus at greater than $10^6$ PFU/ml in unconcentrated culture medium, greater than $10^7$ PFU/ml in unconcentrated culture medium, greater than $10^8$ PFU/ml in unconcentrated culture medium, or greater than $10^9$ PFU/ml in unconcentrated culture medium.

Some embodiments of the present teachings include methods of growing a vector comprising a toxic gene in vitro. In various configurations, these methods comprise providing a cell culture comprising insect cells, infecting or transfecting the cells with a nucleic acid of the present teachings which comprises a sequence encoding a toxic polypeptide and an intron which interrupts the sequence, and incubating the cells under conditions suitable for virus production. In various configurations, a nucleic acid can be comprised by a virus, such as a baculovirus, an AAV, or a combination thereof. Accordingly, in various configurations, these methods include: providing a cell culture comprising insect cells; and infecting the cells with a virus vector such as an AAV comprising a nucleic acid of the present teachings, and with a second vector such as Bac-inCap-inRep. The infecting can occur over at least about 1 day, for at least 2 days, for at least 3 days, for about 3 days, for at least 4 days, for at least 5 days, for up to about 5 days, for at least 6 days, for up to about 6 days, for 7 days, or for up to about 7 days. In various configurations, these methods can further comprise lysing the cells to form a lysate comprising the AAV. Because a lysate can also include cellular debris, the methods can further comprise digesting the cellular debris with benzonase. In various configurations, an AAV comprising a nucleic acid of these methods can be any AAV, such as an AAV2 or an AAV9. In some configurations, the insect cells can be Trichoplusia ni BTI-Tn-5B1-4 cells, Spodoptera frugiperda Sf9 cells or Spodoptera frugiperda Sf21 cells. In some preferred configurations, the insect cells in these methods can be Spodoptera frugiperda Sf9 cells.

Some embodiments of the present teachings include methods of treating a disease or medical condition such as HIV infection, graft-versus-host disease, or cancer. In various configurations, these methods can comprise administering to a subject in need of therapy a therapeutically effective amount of a nucleic acid of the present teachings. In various configurations, the nucleic acid can be comprised by a virus, such as AAV, so that the methods comprise administering to a subject in need of therapy a therapeutically effective amount of a virus such as an AAV comprising a nucleic acid of the present teachings. In some preferred embodiments, the AAV can be AAV2 or AAV9, more preferably AAV2. In various configurations, a cancer that can be treated by the disclosed methods can be, without limitation, a prostate cancer, a breast cancer, a brain tumor, a cervical cancer or a nasopharyngeal carcinoma.

Some embodiments of the present teachings include use of a nucleic acid or virus of the present teachings for the treatment of HIV infection, graft-versus-host disease, or a cancer.

Some embodiments of the present teachings include a nucleic acid or virus of the present teachings for use in the treatment of HIV infection, graft-versus-host disease, or a cancer.

Some embodiments of the present teachings include a nucleic acid or virus of the present teachings for use in the treatment of HIV infection, graft-versus-host disease, or a cancer.

BRIEF DESCRIPTION OF THE DRAWINGS

FIG. 6 illustrates a map of pFastBac shuttle plasmid comprising, between AAV ITR's, a CMV promoter operably linked to a DT-A coding sequence in which the vector comprises: Tn7R and Tn7L target sites; an ampicillin resistance selection marker; a gentamicin resistance selection marker; an hGH intron that is not within a coding sequence; AAV ITR's; and an SV40pA 144 bp polyadenylation sequence. Abbreviations: DT-A, diphtheria A fragment; CMV, cytomegalovirus promoter; hGH, human growth hormone intron.

FIG. 7 illustrates a pFastBac shuttle plasmid comprising, between AAV ITR's, a CMV promoter operably linked to a DT-A coding sequence interrupted by human growth hormone intron, in which the vector comprises: Tn7R and Tn7L target sites; an ampicillin resistance selection marker; a gentamicin resistance selection marker; an hGH intron that is not within a coding sequence; AAV ITR's; and an SV40pA 144 bp polyadenylation sequence. Abbreviations: DT-A, diphtheria A fragment; CMV, cytomegalovirus promoter; hGH, human growth hormone intron; SV40, Simian virus 40 large T-antigen intron.

FIG. 8 illustrates a map of a pFastBac shuttle plasmid comprising, between AAV ITR's, a CMV promoter operably linked to a Barnase coding sequence fused in-frame with GFP coding sequence, in which the vector comprises: Tn7R and Tn7L target sites; an ampicillin resistance selection marker; a gentamicin resistance selection marker; an hGH intron that is not within a coding sequence; AAV ITR's; and an SV40pA 144 bp polyadenylation sequence. Abbreviations: CMV, cytomegalovirus promoter; hGH, human growth hormone intron; Bar, Barnase; GFP, green fluorescence protein; SV40, Simian virus 40 large T-antigen intron.

FIG. 9 illustrates a map of a pFastBac shuttle plasmid comprising, between AAV ITR's, a CMV promoter operably linked to a Barnase coding sequence interrupted by an SV40 large T-antigen intron, and fused in-frame with GFP coding sequence, in which the vector comprises: Tn7R and Tn7L target sites; an ampicillin resistance selection marker; a gentamicin resistance selection marker; an hGH intron that is not within a coding sequence; AAV ITR's; and an SV40pA 144 bp polyadenylation sequence. Abbreviations: CMV, cytomegalovirus promoter; hGH, human growth hormone intron; Bar, Barnase; GFP, green fluorescence protein; SV40, Simian virus 40 large T-antigen intron.

FIG. 10 illustrates a map of a pFastBac shuttle plasmid comprising, between AAV ITR's, an hTERT promoter operably linked to a DT-A coding sequence interrupted by human growth hormone intron, in which the vector comprises: Tn7R and Tn7L target sites; an ampicillin resistance selection marker; a gentamicin resistance selection marker; an hGH intron that is not within a coding sequence; AAV ITR's; and an SV40pA 144 bp polyadenylation sequence. Abbreviations: DT-A, diphtheria A fragment; hGH, human growth hormone intron; SV40, Simian virus 40 large T-antigen intron; hTERT, human telomerase reverse transcriptase promoter.

FIG. 11 illustrates a map of a pFastBac shuttle plasmid comprising, between AAV ITR's, an hTERT promoter operably linked to a GFP coding sequence, in which the vector comprises: Tn7R and Tn7L target sites; an ampicillin resistance selection marker; a gentamicin resistance selection marker; an hGH intron that is not within a coding sequence; AAV ITR's; and an SV40pA 144 bp polyadenylation sequence. Abbreviations hGH, human growth hormone intron; Bar, Barnase; GFP, green fluorescence protein; SV40, Simian virus 40 large T-antigen intron; hTERT, human telomerase reverse transcriptase promoter.

DETAILED DESCRIPTION

The present teachings disclose a toxic gene comprising an intron, wherein following transcription in an insect cell, the intron is not spliced, so that no toxic gene product is formed in the insect cell. A vector comprising such an intron-interrupted toxic gene can be grown in insect cells. However, upon introduction into a mammalian cell such as a cancer cell, transcription of the toxic gene leads formation of a mature mRNA, which is translated into a toxic protein that kills the host mammalian cell.

Figure 1:
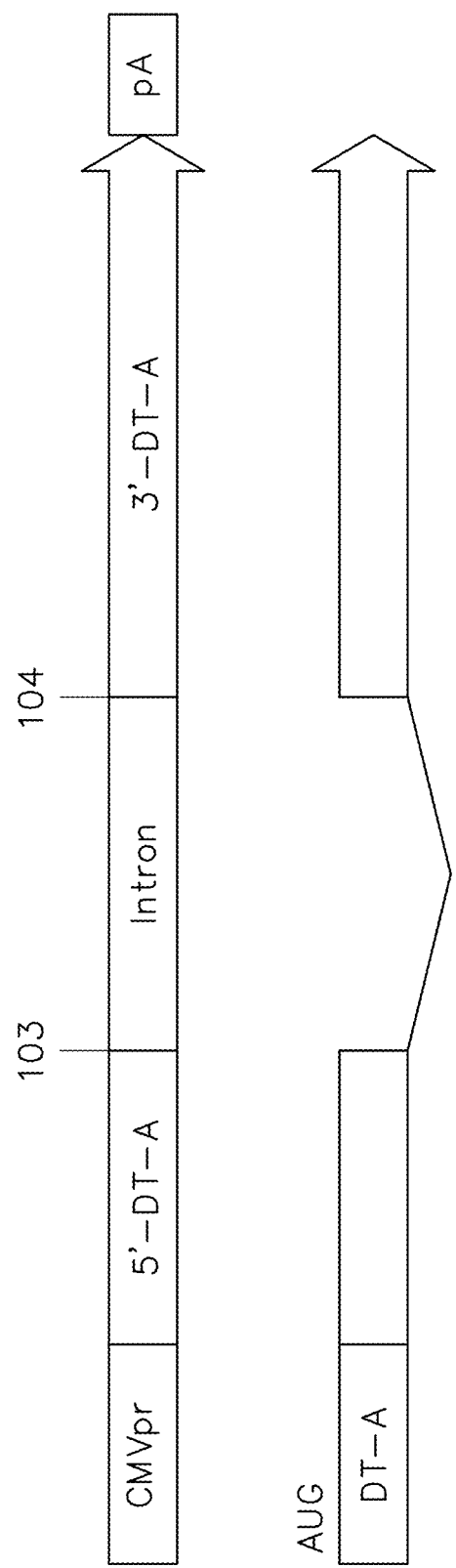
FIG. 1 illustrates genetic and transcriptional maps of a toxic gene such as a DT-A gene comprising an intron and operably linked to a promoter such as a CMV promoter.

FIG. 1 illustrates exemplary genetic and transcriptional maps of a DT-A gene comprising an intron and operably linked to a CMV promoter. Upon introduction of a DT-A gene comprising an intron of the present teachings into a mammalian cell, the gene is transcribed, and mature DT-A mRNA is formed in the mammalian cell through intron splicing. The mature RNA is translated into functional DT-A protein to kill the cell. The numbers above the genetic map based on DT-A coding sequence (Genbank access no. X00703) indicate the nucleotide positions where the intron is inserted. CMVpr=cytomegalovirus promoter; DT-A=Diptheria Toxin A nucleic acid sequence; pA=polyadenylation signal.

The methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Methods In Molecular Biology, ed. Richard, Humana Press, NJ, 1995; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999. Additional references describing methods of expression of heterologous polypeptides in insect cells, as well as methods of introducing vectors and nucleic acids into insect cells and methods of maintaining insect cell cultures include, for example, O'Reilly et al., Baculovirus Expression Vectors, A Laboratory Manual, Oxford Univ. Press, 1994; Samulski et al., J. Vir. 63: 3822-3288, 1989; Kajigaya et al., Proc. Nat'l. Acad. Sci. USA 88: 4646-4650, 1991; Ruffing et al., J. Vir. 66: 6922-6930, 1992; Kimbauer et al., Vir. 219: 37-44, 1996; Zhao et al., Vir. 272: 382-393, 2000; and Samulski et al., U.S. Pat. No. 6,204,059.

Experiments described herein may also make use of the following materials and methods.

Cell culture. HEK293 cells were maintained at 37° C. in Dulbecco's modified Eagle's medium (Invitrogen, Carlsbad, Calif.) containing 100 U/ml of penicillin and 100 mg/ml of streptomycin, and supplemented with 10% fetal calf serum (Sigma-Aldrich, St. Louis, Mo.). HepG2, Hep3B and WI38 cells were maintained at 37° C. in EMEM complete growth medium (American Type Culture Collection) containing 100 U/ml of penicillin and 100 mg/ml of streptomycin, and supplemented with 10% fetal calf serum. BE (2) M17 cells (American Type Culture Collection) were maintained in 50% EMEM+50% F12 complete growth media containing 100 U/ml of penicillin and 100 mg/ml of streptomycin, and supplemented with 10% fetal calf serum. *Spodoptera frugiperda* Sf9 cells (Invitrogen, Carlsbad, Calif.) were maintained at 28° C. in ESF921 serum-free medium (Expression Systems, Woodland, Calif.) containing 100 U/ml of penicillin and 100 mg/ml of streptomycin (Invitrogen, Carlsbad, Calif.).

Generation and titration of recombinant baculoviruses. Plasmids constructed as described above were used for transforming DH10Bac-competent cells to generate recombinant bacmids. The bacmids containing the target genes were used for generating recombinant baculoviruses in accordance with the manufacturer's protocol (Invitrogen, Carlsbad, Calif.), with minor modifications. Briefly, 2 ng of the plasmid DNA was used for transforming 20 µl of DH10Bac-competent cells. After 4 hours of incubation at 37° C. in 500 µl of SOC medium, 25 and 2.5 µl of the culture were plated separately in selection plates and incubated for 48 hours to allow white/blue colonies to form. Generally, three white colonies were picked for each construct and miniprep bacmid DNAs were prepared. The bacmid DNAs were used for transfecting Sf9 cells to generate recombinant baculoviruses. The recombinant baculoviruses were amplified once and titers determined with real-time quantitative PCR (qPCR) assay and converted to plaque-forming units (pfu) based on empirical studies in which 20 copies was converted into 1 pfu.

AAV vector production, purification and titration. The methods for AAV vector production, purification and titration have been described previously (Chen, H., Mol Ther 16: 924-930, 2008). Briefly, Sf9 cells were grown at 28° C. to $\sim 1 \times 10^7$ cells/ml in ESF921 serum-free medium containing 100 U/ml of penicillin and 100 µg/ml of streptomycin, and diluted to $\sim 5 \times 10^6$ cells/ml before infection. Double infection was employed to produce AAV vectors. Five multiplicity of infection (moi) of Bac-AAV-transgene, and 10 moi of Bac-inCap-inRep were used to infect Sf9 cells at 28° C. for 3 days to produce AAV vectors. After 3 days of infection, cell pellets were collected by centrifugation at 3,000 rpm for 15 minutes. The cell pellets were lysed in a modified Sf9 lysis buffer (50 mM Tris-HCl, pH8.0, 1% sarkosyl, 1% Triton X-100, 2 mM $MgCl_2$) and cellular nucleic acids (DNA and RNA) were digested using benzonase (Sigma-Aldrich, St. Louis, Mo.). The cell lysates were cleared by centrifugation at 8,000 rpm for 20 min and supernatants were subjected to 2 rounds of ultracentrifugation to purify the AAV vectors. The AAV vectors were buffer-exchanged into PBS containing 0.001% pluronic F-68 (Sigma-Aldrich, St. Louis, Mo.) with 2 PD-10 desalting columns (GE HealthCare Bio-Science Corp, Piscataway, N.J.). After purification, the AAV vectors were titrated with real-time quantitative PCR (qPCR) method.

Cell proliferation assay. HEK293 cells were grown in 24-well plate (1.5e+5 cells/well) overnight and transduced with AAV2 vectors (1.5e+9 vg/well) for 48 hours. The cells were then trypsinized and cell number counted. The cells were further cultivated for another 48 hours until reaching confluency and trypsinized, cell number counted and then expand into larger vessels. After another 72 hour cultivation, the cells were trypsinized and counted. Viable cells were counted with trypan blue staining.

Cell viability assay. The CellTiter Glo Luminescent Cell Viability Assay kit was used to test the cell viability according to Manufacturer's protocol (Promega, Madison, Wis.). Briefly, the cells (WI38, HepG2, Hep3B, and BE (2) M17) were seeded on 96-well plates at 3.2e+4 cells/well overnight and transduced with AAV2 vectors at 4-fold serial dilutions for 4 days. The reagent was reconstituted and added to the cells. After mixing on an orbital shaker for 2 minutes to lyse the cells, the plate was incubated at room temperature for 10 minutes and then the luminescent signals were recorded.

As used in the description, drawings and any appended claims, the singular forms "a", "an" and "the" are intended to include the plural forms as well, unless the context indicates otherwise.

The present inventor has developed compositions and methods for producing a vector comprising a toxic gene in an insect cell, as well as insect cell cultures that can include a vector comprising a toxic gene, and can produce virus such as an AAV to a titer of at least $10^9$ viral genomes/ml, at least $10^{10}$ viral genomes/ml, at least $10^{11}$ viral genomes/ml or at least $10^{12}$ viral genomes/ml, in unconcentrated culture medium. In various configurations, a cell culture can produce a baculovirus to a titer of at least $10^6$ plaque forming units (PFU)/ml, at least $10^7$ PFU/ml, at least $10^8$ PFU/ml, at least $10^9$ PFU/ml or at least $10^{10}$ PFU/ml, in unconcentrated culture medium.

Insect cells that can be used in various configurations of the present teachings can be any insect cells that can grow in an in vitro culture. Such cells are well known to skilled artisans and include, without limitation, those disclosed in Kost, T. A., et al., Nature Biotechnology 23: 567-575, 2005, and references cited therein.

EXAMPLES

The following examples are illustrative of various embodiments of the present teachings and are not intended to limit the scope of any claim. Persons of skill in the art will recognize that many variations are possible that are within the scope of the present teachings.

Example 1

Figure 6:
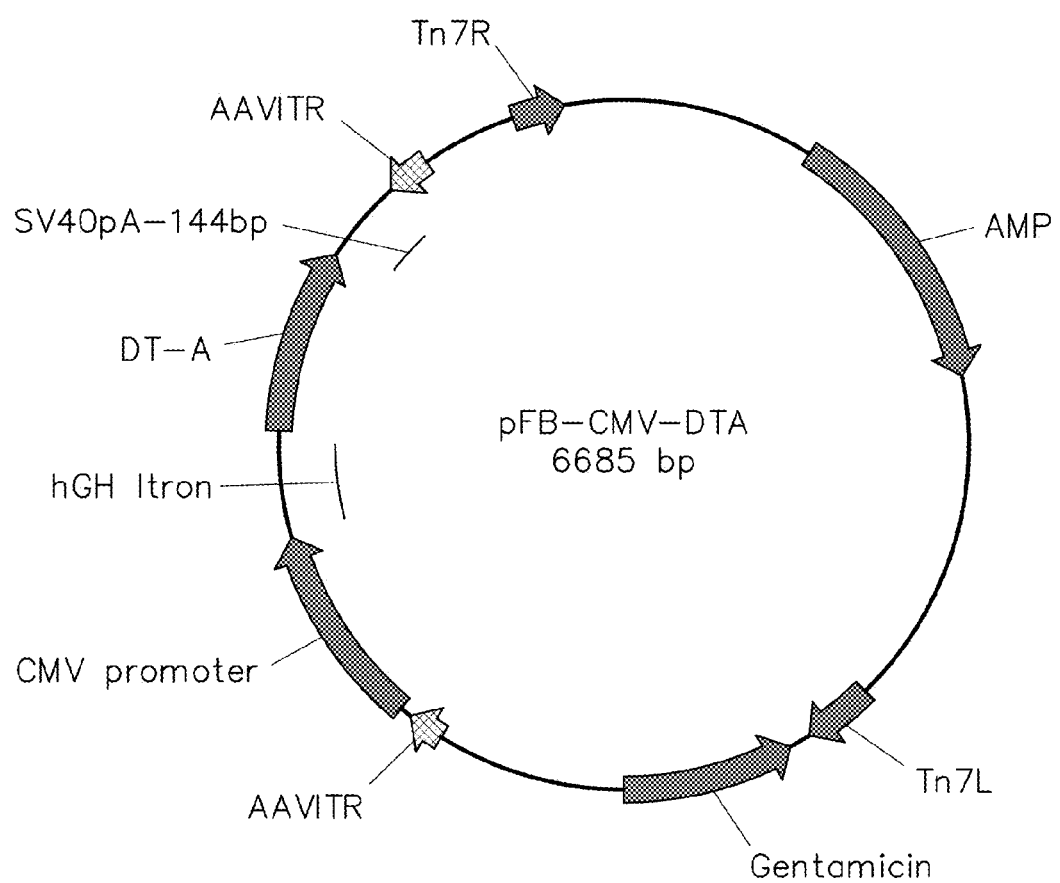
FIGS. 6-11 illustrate maps of pFastBac shuttle plasmids that can be used in various configurations of the present teachings. Each vector comprises: Tn7R and Tn7L target sites; an ampicillin resistance selection marker (AMP); a gentamicin resistance selection marker; an hGH intron that is not within a coding sequence; AAV ITR's; and an SV40pA 144 bp polyadenylation sequence, CATGGCCCAACT-TGTTTATTGCAGCTTATAATGGTTA-CAAATAAAGCAATAGCATCA CAAATTTCACAA ATAAAGCATTTTTTTCACTGCAT-TCTAGTTGTGGTTTGTCCAAACT CATCAATGTATCT-TATCATGTCTGGATCT (SEQ ID NO: 1). However, these components individually may not be required for practicing the various embodiments of the present teachings. Abbreviations: DT-A, diphtheria A fragment; CMV, cytomegalovirus promoter; hGH, human growth hormone intron; Bar, Barnase; GFP, green fluorescence protein; SV40, Simian virus 40 large T-antigen intron; hTERT, human telomerase reverse transcriptase promoter.

This example illustrates structure and construction of plasmid pFB-CMV-DTA, a pFastBac shuttle plasmid (Invitrogen Corporation, Carlsbad, Calif.) comprising a CMV promoter operably linked upstream to a DT-A coding sequence (FIG. 6).

Figure 7:
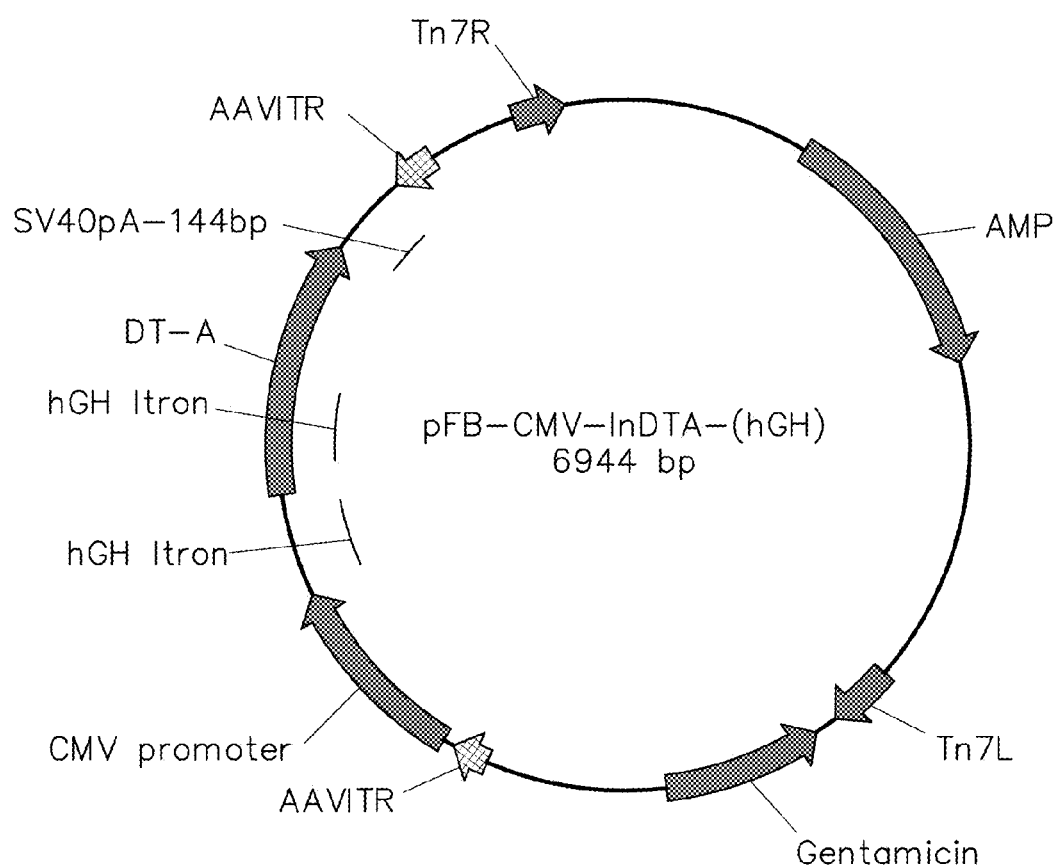

To construct this plasmid, a plasmid containing the DT-A gene (GenBank access no. X00703) was digested with restriction endonucleases EcoRI and BamHI to generate a fragment containing a DT-A coding sequence with EcoRI and BamHI sticky ends. This fragment was ligated to the EcoRI and BamHI sites of plasmid pFB-AAV-CMV-SV40pA to create pFB-CMV-DTA. To insert the human growth hormone intron into the DT-A gene, a PCR method was employed. First, the upstream junction sequence together with the 5'-DT-A sequence from nucleotide numbers 1 to 103 were amplified using forward primer 5'-GATTATGATCAC-TAGTCGAG-3' (SEQ ID NO: 2) and reverse primer 5'-GGGCGCTTACCTTTTTGAATGGAATCTACA-3' (SEQ ID NO: 3) (bold typeface indicates human growth hormone intron sequence). The human growth hormone intron was amplified with forward primer 5'-ATTCAAAAAGG-TAAGCGCCCCTAAAATCCC-3' (SEQ ID NO: 4) (bold typeface indicates human growth hormone intron sequence) and reverse primer 5'-TTTTGTATACCTGGGGAGAAAC-CAGAGGGC-3' (SEQ ID NO: 5) (italic typeface indicates restriction site for BstZ17I; bold typeface indicates human growth hormone intron sequence). These two PCR fragments were then joined together through a second PCR amplification with forward primer 5'-GATTATGATCACTAGTC-GAG-3' (SEQ ID NO: 6) and reverse primer 5'-TTTTG-TATACCTGGGGAGAAACCAGAGGGC-3' (SEQ ID NO: 7). The joined PCR fragment was then digested with restriction endonucleases EcoRI and BstZ17I and ligated to the EcoRI and BstZ17I sites of pFB-CMV-DTA to create pFB-CMV-inDTA (hGH) (FIG. 1, FIG. 7), and to the EcoRI and BstZ17I sites of pFB-CMVtetO-DTA-p10-TetR to create pFB-CMVtetO-inDTA-p10-TetR. The expression cassette was verified by DNA sequencing analysis.

The DNA sequence of the DT-A gene (GenBank access no. X00703) used in this example is:

(SEQ ID NO: 8)
```
gtgagcagaaaactgtttgcgtcaatcttaatagggg cgctactggggatagggg ccccaccttcagcccatgcaggcgctgatgatgttgt tgattcttctaaatatttgtgatggaaaacttttcttcgtaccacgggactaaacctggttatgtagattccattcaaaaaggtatacaaaagcca aaatctggtacacaaggaaattatgacgatgattggaaagggttttatagtaccgacaataaatacgacgctgcgggatactctgtagataat gaaacccgctctctggaaaagctggaggcgtggtcaaagtgacgtatccaggactgacgaaggttctcgcactaaaagtggataatgcc gaaactattaagaaagagttaggtttaagtctcactgaaccgttgatggagcaagtcggaacggaagagtttatcaaaaggttcggtgatggt gcttcgcgtgtagtgctcagccttcccttcgctgaggggagttctagcgttgaatatattaataactgggaacaggcgaaagcgttaagcgta gaacttgagattaattttgaaacccgtggaaaacgtggccaagatgcgatgtatgagtatatggctcaagcctgtgcaggaaatcgtgtcag gcgatcagtaggtagctcattgtcatgcataaatcttgattgggatgtcataagggataaaactaagacaaagatagagtctttgaaagagca tggccctatcaaaaataaaatgagcgaaagtcccaataaaacagtatctgaggaaaaagctaaacaatacctagaagaatttcatcaaacg gcattagagcatcctgaattgtcagaacttaaaaccgttactgggaccaatcctgtattcgctggggctaactatgcggcgtgggcagtaaac gttgcgcaagttatcgatagcgaaacagctgataatttggaaaagacaactgctgctctttcgatacttcctggtatcggtagcgtaatgggca ttgcagacggtgccgttcaccacaatacagaagagatagtggcacaatcaatagctttatcgtctttaatggttgctcaagctattccattggta ggagagctagttgatattggtttcgctgcatataatttgtagagagtattatcaatttatttcaagtagttcataattcgtataatcgtcccgcgtat tctccggggcataaaacgcaaccatttcttcatgacgggtatgctgtcagttggaacactgttgaagattcgataatccgaactggttttcaag gggagagtgggcacgacataaaaattactgctgaaaataccccgcttccaatcgcgggtgtcctactaccgactattcctggaaagctgga cgttaataagtccaagactcatatttccgtaaatggtcggaaaataaggatgcgttgcagagctatagacggtgatgtaactttttgtcgccta aatctcctgtttatgttggtaatggtgtgcatgcgaatcttcacgtggcatttcacagaagcagctcggagaaaattcattctaatgaaatttcgt cggattccataggcgttcttgggtaccagaaaacagtagatcacaccaaggttaattctaagctatcgctattttttgaaatcaaaagctga.
```

DT-A coding sequence comprising the hGH intron is as follows:

(SEQ ID NO: 39)
```
ATGGGCGCTGATGATGTTGTTGATTCTTCTAAATCTTTTGTGATGGAAAACTTTTCTT

CGTACCACGGGACTAAACCTGGTTATGTAGATTCCATTCAAAAAGgtaagcgcccctaaaatc cctttggcacaatgtgtcctgaggggagaggcagcgacctgtagatgggacggggcactaaccctcagggtttggggttctgaatgtga gtatcgccatgtaagcccagtatttggccaatctcagaaagctcctggctccctggaggatggagagagaaaaacaaacagctcctggag
```

```
cagggagagtgctggcctcttgctctccggctccctctgttgccctctggtttctccccagGTATACAAAAGCCAAAATCT
GGTACACAAGGAAATTATGACGATGATTGGAAAGGGTTTTATAGTACCGACAATAA
ATACGACGCTGCGGGATACTCTGTAGATAATGAAAACCCGCTCTCTGGAAAAGCTG
GAGGCGTGGTCAAAGTGACGTATCCAGGACTGACGAAGGTTCTCGCACTAAAAGTG
GATAATGCCGAAACTATTAAGAAAGAGTTAGGTTTAAGTCTCACTGAACCGTTGAT
GGAGCAAGTCGGAACGGAAGAGTTTATCAAAAGGTTCGGTGATGGTGCTTCGCGTG
TAGTGCTCAGCCTTCCCTTCGCTGAGGGGAGTTCTAGCGTTGAATATATTAATAACT
GGGAACAGGCGAAAGCGTTAAGCGTAGAACTTGAGATTAATTTTGAAACCCGTGGA
AAACGTGGCCAAGATGCGATGTATGAGTATATGGCTCAAGCCTGTGCAGGAAATCG
TGTCAGGCGATGA.
```

Example 2

This example illustrates structure and construction of plasmid pFB-CMVtetO-DTA-p10-TetR. To construct pFB-CMVtetO-DTA-p10-TetR, a p10-driven TetR expression cassette was released from a plasmid by digestion with restriction endonucleases HindIII and AvrII. The released fragment was inserted into HindIII and AvrII sticky ends of plasmid pFB-CMV-DTA that had been digested with restriction endonucleases HindIII and AvrII.

Example 3

This example illustrates insertion of mammalian introns to disrupt toxin gene ORFs.

To generate the vectors of some embodiments of the present teachings, the human growth hormone (hGH) intron was inserted into the DT-A ORF between nucleotides 103 and 104 (the first letter of start codon ATG is assigned as nucleotide No. 1). The SV40 large T antigen (SV40LT) intron was inserted into the barnase ORF between nucleotides 9 and 10. The DT-A and barnase ORFs without intron interruption were used as controls. All the toxin coding sequences with or without intron interruption were cloned into the pFastBac shuttle plasmid and the schematic depiction of the expression cassettes are shown in FIG. 3.

Figure 3A:
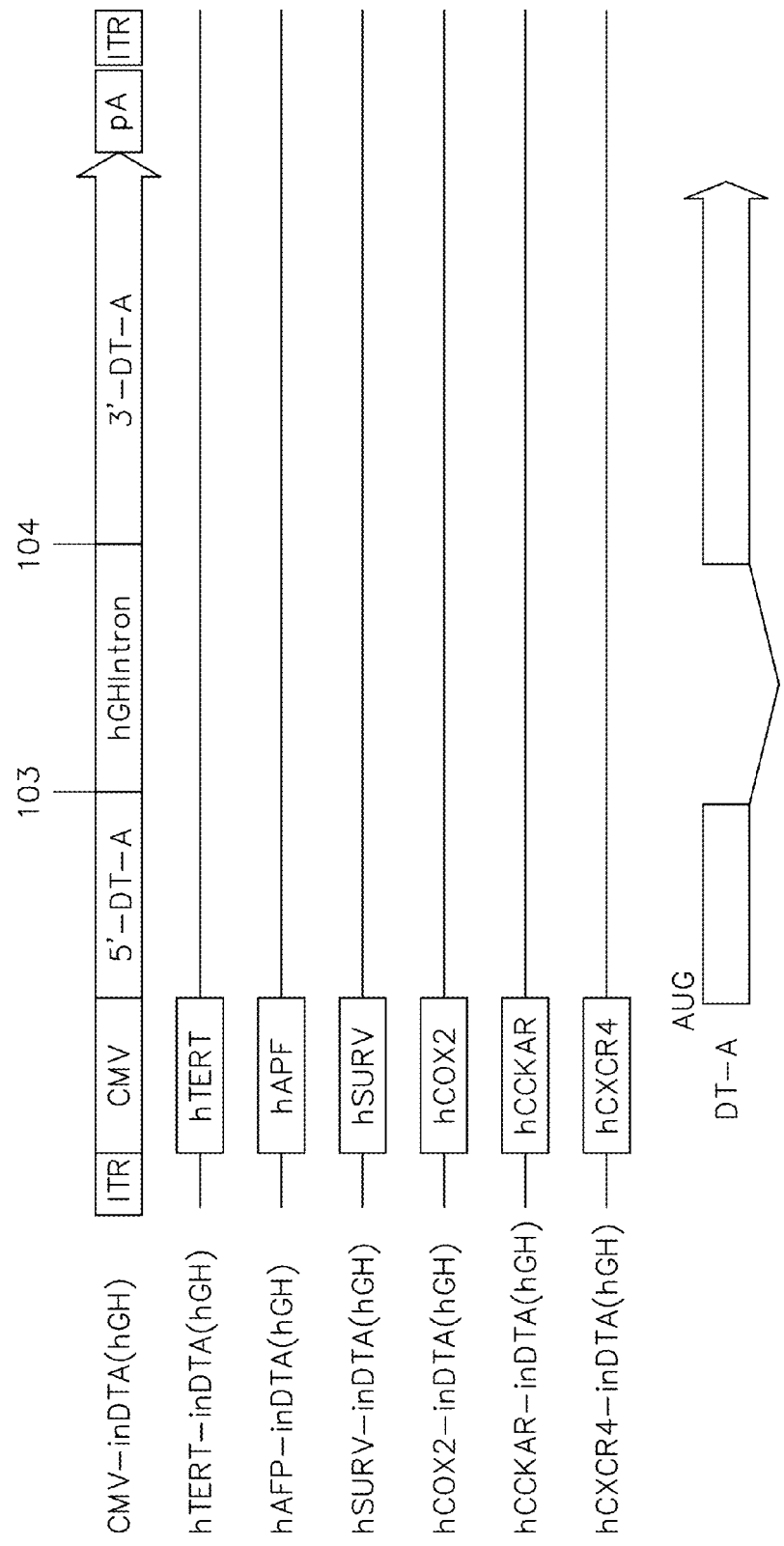
FIG. 3 illustrates genetic and transcriptional maps of representative AAV vectors carrying a toxic gene such as a DT-A gene, modified to comprise an intron within the open reading frame.
Figure 3B:
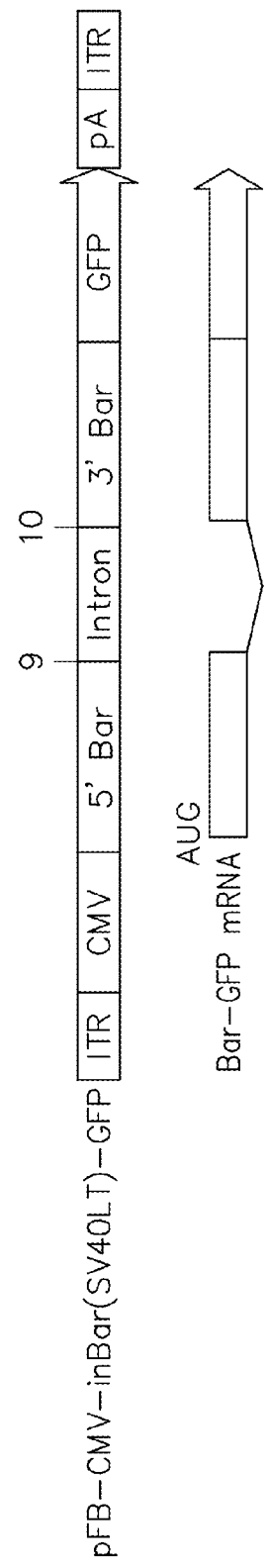
Figure 3C:
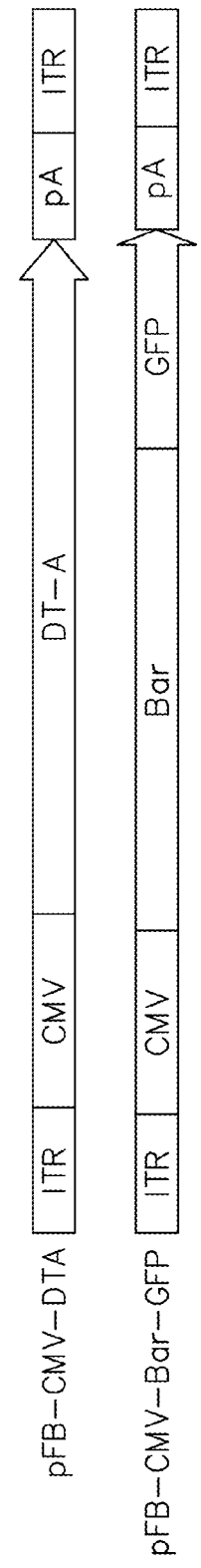
Figure 4:
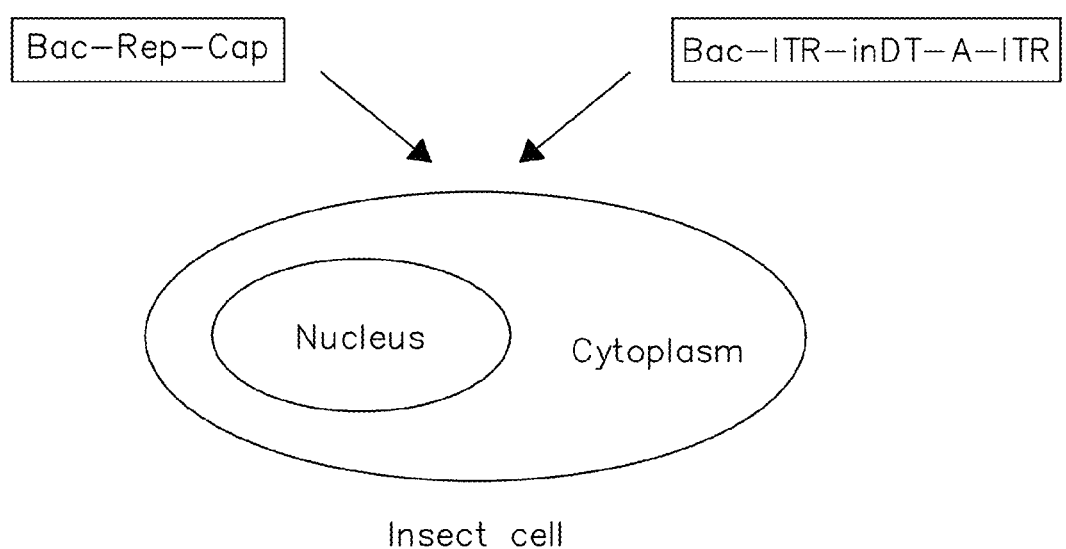
FIG. 4 illustrates a method of producing AAV vectors carrying a toxic gene such as a DT-A gene in insect cells.
Figure 5:
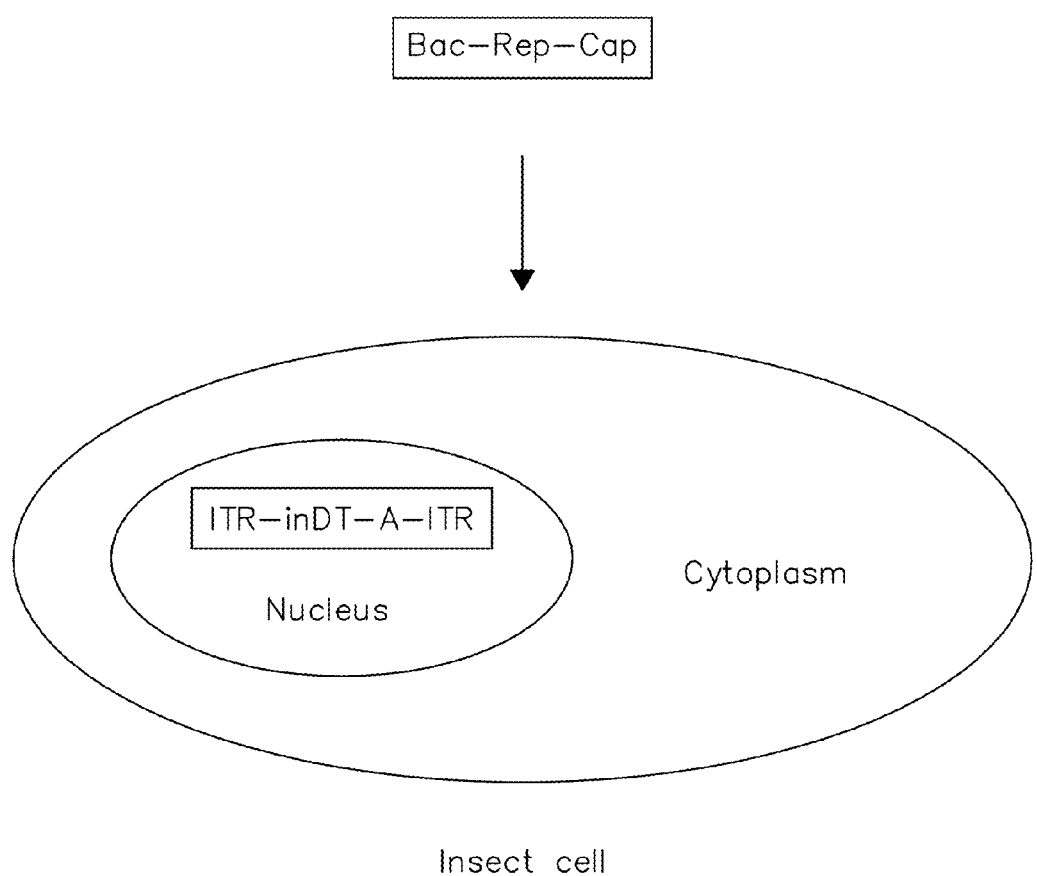
FIG. 5 illustrates an alternative method of producing AAV vectors carrying a toxic gene such as a DT-A gene comprising of an intron in insect cells with stably integrated AAV-transgene. Bac, Rep, Cap and ITR are as described in US Patent Application Publication 20090203071.

FIG. 3 illustrates genetic and transcriptional maps of representative recombinant baculoviruses carrying the toxin expression cassettes flanked by AAV ITRs. AAV vectors were produced by co-infecting insect cells with a second recombinant baculovirus carrying AAV rep and cap genes. Upon introduction of the baculoviral or AAV vectors into a mammalian cell, mature toxin mRNA is formed through intron splicing and translated into functional protein to kill the cell. (a) DT-A gene inserted with hGH intron and under control of various tumor specific promoters. The numbers above the genetic map based on DT-A coding sequence (Genbank access no. X00703) indicate the nucleotide positions where the intron is inserted. (b) Barnase gene inserted with SV40LT antigen intron and fused in-frame with GFP gene. The numbers above the genetic map are based on barnase coding sequence (Genbank access no. M14442), and indicate the nucleotide positions where the intron is inserted. (c) DT-A and barnase genes without intron insertion.

The detailed sequence of barnase coding sequence comprising the SV40LT antigen intron is as follows.

(SEQ ID NO: 40)
```
ATGGCACAGgtatttgcttcttccttaaatcctggtgttgatgcaatgtactgcaaacaatggcctgagtgtgcaaagaaaatgtctgct
aactgcatatgcttgctgtgcttactgaggatgaagcatgaaaatagaaaattatacaggaaagatccacttgtgtgggttgattgctactgctt
cgattgctttagaatgtggtttggacttgatctttgtgaaggaaccttacttctgtggtgtgacataattggacaaactacctacagagatttaaa
gctctaaggtaaatataaaattttttaagtgtataatgtgttaaactactgattctaattgtttgtgtattttagGTTATCAACACGTTTG
ACGGGGTTGCGGATTATCTTCAGACATATCATAAGCTACCTGATAATTACATTACAA
AATCAGAAGCACAAGCCCTCGGCTGGGTGGCATCAAAAGGGAACCTTGCAGACGTC
GCTCCGGGGAAAAGCATCGGCGAGACATCTTCTCAAACAGGGAAGGCAAACTCC
AGGGCAAAAGCGGACGAACATGGCGTGAAGCGGATATTAACTATACATCAGGCTTC
AGAAATTCAGACCGGATTCTTTACTCAAGCGACTGGCTGATTTACAAAACAACGGA
CCATTATCAGACCTTTACAAAAATCAGAATGGTGAGCAAGGGC.
```

(SEQ ID NO: 41)
Fused with GFP, the added sequence is - - - GFP - - - GAGCTGTACAAGTAA.

Example 4

Figure 8:
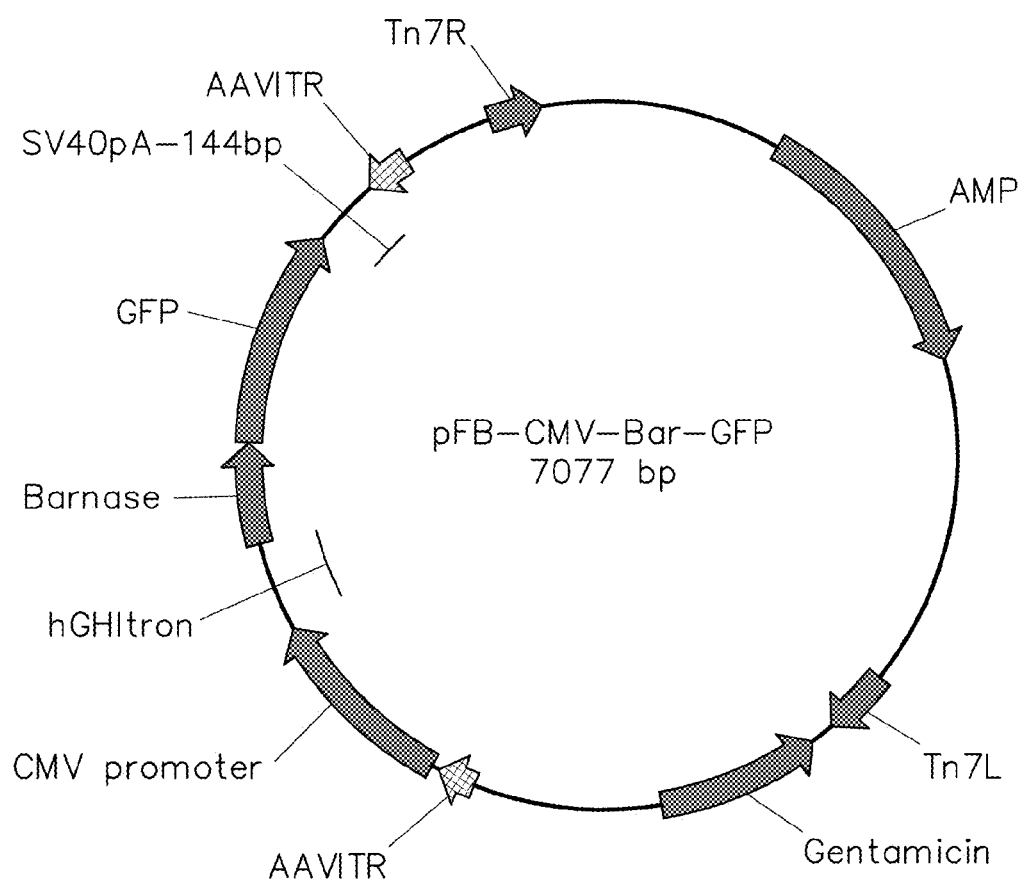

This example illustrates structure and construction of plasmid pFB-CMV-Bar-GFP comprising a CMV promoter operably linked upstream to a barnase coding sequence fused in-frame with a green fluorescent protein (GFP) coding sequence (FIG. 8).

To construct pFB-CMV-Bar-GFP (FIG. 8), barnase coding sequence (GenBank access no. M14442) was amplified from plasmid pF1A-T7 (Promega, Madison Wis.) with forward primer 5'-CCCGAATTCGCCACCATGGCACAGGT-TATCAAC-3' (SEQ ID NO: 9) (italic typeface indicates restriction site for EcoRI) and reverse primer 5'-TGCTCAC-CATTCTGATTTTTGTAAAGGTCT-3' (SEQ ID NO: 10). The GFP coding sequence (GenBank access no. U55762) was amplified from pFB-GFP plasmid with forward primer 5'-CAAAAATCAGAATGGTGAGCAAGGGCGAGG-3' (SEQ ID NO: 11) and reverse primer 5'-GGGGGGTACCT-CATTACTTGTACAGCTCGTCC-3' (SEQ ID NO: 12) (italic typeface indicates restriction site for KpnI). A second round of PCR was performed to fuse Barnase coding sequence with GFP coding sequence together using forward primer 5'-CCCGAATTCGCCACCATGGCACAGGT-TATCAAC-3' (SEQ ID NO: 13) and reverse primer 5'-GGGGGGTACCTCATTACTTGTACAGCTCGTCC-3' (SEQ ID NO: 14). The fused PCR fragment was digested with restriction endonucleases EcoRI and KpnI and ligated to the EcoRI and KpnI sites of pFB-CMV-inDTA (hGH) to replace the DT-A sequence and create pFB-CMV-Bar-GFP.

DNA sequence of a barnase gene used in this example (GenBank access no. M14442) is:

```
                                                                    (SEQ ID NO: 15)
ctggaaaacgtcacattgcttccgcatatcgggtcagcaacggctaaaatccgcttgaatatgttcacacaagccgctcaaaacatgattgac gccgtatacggaagaacgccgaaaaaccttactaaggaatttcaataagaagaaaaatcccggttggttcagccggggtttattttcgctag ataaaaagtactatttttaaattctttctattcctttctttcgttgctgatacaatgaaaaggaatcagcttcacatgatgaaaatgggaggtattgct ttgaaaaaacgattatcgtggatttccgtttgtttactggtgcttgtctccgcggcggggatgctgttttcaacagctgccaaaacggaaacatc ttctcacaaggcacacacagaagcacaggttatcaacacgtttgacggggttgcggattatcttcagacatatcataagctacctgataattac attacaaaatcagaagcacaagccctcggctgggtggcatcaaaagggaaccttgcagacgtcgctccggggaaaagcatcggcggag acatcttctcaaacagggaaggcaaactcccgggcaaaagcggacgaacatggcgtgaagcggatattaactatacatcaggcttcagaa attcagaccggattctttactcaagcgactggctgatttacaaaacaacggaccattatcagacctttacaaaaatcagataacgaaaaaaac ggcttccctgcggaggccgttttttttcagctttacataaagtgtgtaataaatttttcttcaaactctgatcggtcaatttcacttt.
```

The DNA sequence of a GFP gene used in this example is:

```
                                                                    (SEQ ID NO: 16)
tagttattaatagtaatcaattacggggtcattagttcatagcccatatatggagttccgcgttacataacttacggtaaatggcccgcctggctg accgcccaacgaccccgcccattgacgtcaataatgacgtatgttcccatagtaacgccaataggactttccattgacgtcaatgggtgg agtatttacggtaaactgcccacttggcagtacatcaagtgtatcatatgccaagtacgccccctattgacgtcaatgacggtaaatggcccg cctggcattatgcccagtacatgaccttatgggactttcctacttggcagtacatctacgtattagtcatcgctattaccatggtgatgcggttttg gcagtacatcaatgggcgtggatagcggtttgactcacggggatttccaagtctccaccccattgacgtcaatgggagtttgttttggcacca aaatcaacgggactttccaaaatgtcgtaacaactccgccccattgacgcaaatgggcggtaggcgtgtacggtgggaggtctatataagc agagctggtttagtgaaccgtcagatccgctagcgctaccggactcagatctcgagctcaagcttcgaattctgcagtcgacggtaccgcg ggcccgggatccaccggtcgccaccatggtgagcaagggcgaggagctgttcaccggggtggtgcccatcctggtcgagctggacgg cgacgtaaacggccacaagttcagcgtgtccggcgagggcgagggcgatgccacctacggcaagctgaccctgaagttcatctgcacc accggcaagctgcccgtgccctggcccaccctcgtgaccaccctgacctacggcgtgcagtgcttcagccgctaccccgaccacatgaa gcagcacgacttcttcaagtccgccatgcccgaaggctacgtccaggagcgcaccatcttcttcaaggacgacggcaactacaagacccg cgccgaggtgaagttcgagggcgacaccctggtgaaccgcatcgagctgaagggcatcgacttcaaggaggacggcaacatcctggg gcacaagctggagtacaactacaacagccacaacgtctatatcatggccgacaagcagaagaacggcatcaaggtgaacttcaagatcc gccacaacatcgaggacggcagcgtgcagctcgccgaccactaccagcagaacacccccatcggcgacggccccgtgctgctgcccg acaaccactacctgagcacccagtccgccctgagcaaagaccccaacgagaagcgcgatcacatggtcctgctggagttcgtgaccgcc gccgggatcactctcggcatggacgagctgtacaagtaaagcggccgcgactctagatcataatcagccataccacatttgtagaggtttta cttgctttaaaaaacctcccacacctcccctgaacctgaaacataaaatgaatgcaattgttgttgttaacttgtttattgcagcttataatggtta caaataaagcaatagcatcacaaatttcacaaataaagcatttttttcactgcattctagttgtggtttgtccaaactcatcaatgtatcttaaggc
```

-continued

```
gtaaattgtaagcgttaatattttgttaaaattcgcgttaaattttttgttaaatcagctcatttttaaccaataggccgaaatcggcaaaatcccttaa taaatcaaaagaatagaccgagatagggttgagtgttgttccagtttggaacaagagtccactattaaagaacgtggactccaacgtcaaag ggcgaaaaaccgtctatcagggcgatggcccactacgtgaaccatcaccctaatcaagttttttggggtcgaggtgccgtaaagcactaaat cggaaccctaaaggagccccgatttagagcttgacggggaaagccggcgaacgtggcgagaaaggaagggaagaaagcgaaag gagcgggcgctagggcgctggcaagtgtagcggtcacgctgcgcgtaaccaccacacccgccgcgcttaatgcgccgctacagggcg cgtcaggtggcacttttcggggaaatgtgcgcggaacccctatttgtttattttttctaaatacattcaaatatgtatccgctcatgagacaataac cctgataaatgcttcaataatattgaaaaaggaagagtcctgaggcggaaagaaccagctgtggaatgtgtgtcagttagggtgtggaaagt ccccaggctccccagcaggcagaagtatgcaaagcatgcatctcaattagtcagcaaccaggtgtggaaagtccccaggctccccagca ggcagaagtatgcaaagcatgcatctcaattagtcagcaaccatagtcccgcccctaactccgcccatcccgcccctaactccgccagtt ccgcccattctccgccccatggctgactaatttttttatttatgcagaggccgaggccgcctcggcctctgagctattccagaagtagtgagg aggcttttttggaggcctaggcttttgcaaagatcgatcaagagacaggatgaggatcgtttcgcatgattgaacaagatggattgcacgca ggttctccggccgcttgggtggagaggctattcggctatgactgggcacaacagacaatcggctgctctgatgccgccgtgttccggctgt cagcgcaggggcgcccggttcttttttgtcaagaccgacctgtccggtgccctgaatgaactgcaagacgaggcagcgcggctatcgtggc tggccacgacgggcgttccttgcgcagctgtgctcgacgttgtcactgaagcgggaagggactggctgctatttgggcgaagtgccgggg caggatctcctgtcatctcaccttgctcctgccgagaaagtatccatcatggctgatgcaatgcggcggctgcatacgcttgatccggctacc tgcccattcgaccaccaagcgaaacatcgcatcgagcgagcacgtactcggatggaagccggtcttgtcgatcaggatgatctggacgaa gagcatcaggggctcgcgccagccgaactgttcgccaggctcaaggcgagcatgcccgacgcgaggatctcgtcgtgacccatggcg atgcctgcttgccgaatatcatggtggaaaatggccgcttttctggattcatcgactgtggccggctgggtgtggcggaccgctatcaggac atagcgttggctacccgtgatattgctgaagagcttggcggcgaatgggctgaccgcttcctcgtgctttacggtatcgccgctcccgattcg cagcgcatcgccttctatcgccttcttgacgagttcttctgagcgggactctggggttcgaaatgaccgaccaagcgacgcccaacctgcca tcacgagatttcgattccaccgccgccttctatgaaaggttgggcttcggaatcgttttccgggacgccggctggatgatcctccagcgcgg ggatctcatgctggagttcttcgcccacctagggggaggctaactgaaacacggaaggagacaataccggaaggaaccccgcgctatga cggcaataaaaagacagaataaaacgcacggtgttgggtcgtttgttcataaacgcggggttcggtcccagggctggcactctgtcgatac cccaccgagacccattggggccaatacgcccgcgtttcttccttttccccacccaccccccaagttcgggtgaaggcccagggctcgc agccaacgtcggggcggcaggccctgccatagcctcaggttactcatatatactttagattgatttaaaacttcattttttaatttaaaaggatcta ggtgaagatcctttttgataatctcatgaccaaaatcccttaacgtgagttttcgttccactgagcgtcagaccccgtagaaaagatcaaagga tcttcttgagatccttttttttctgcgcgtaatctgctgcttgcaaacaaaaaaaccaccgctaccagcggtggtttgtttgccggatcaagagcta ccaactctttttccgaaggtaactggcttcagcagagcgcagataccaaatactgtccttctagtgtagccgtagttaggccaccacttcaaga actctgtagcaccgcctacatacctcgctctgctaatcctgttaccagtggctgctgccagtggcgataagtcgtgtcttaccgggttggactc aagacgatagttaccggataaggcgcagcggtcgggctgaacggggggttcgtgcacacagcccagcttggagcgaacgacctacacc gaactgagatacctacagcgtgagctatgagaaagcgccacgcttcccgaagggagaaaggcggacaggtatccggtaagcggcagg gtcggaacaggagagcgcacgagggagcttccaggggaaacgcctggtatctttatagtcctgtcgggtttcgccacctctgacttgagc gtcgatttttgtgatgctcgtcaggggggcggagcctatggaaaaacgccagcaacgcggcctttttacggttcctggccttttgctggccttt tgctcacatgttctttcctgcgttatcccctgattctgtggataaccgtattaccgccatgcat.
```

Example 5

Figure 9:
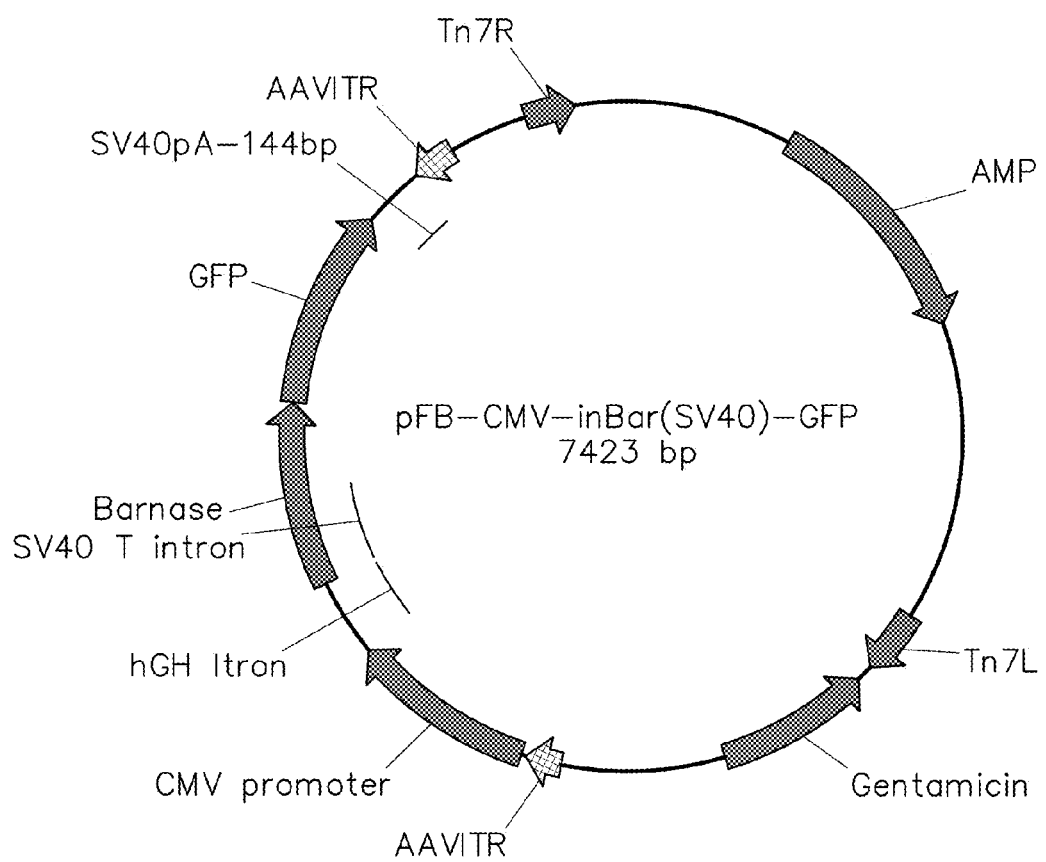

This example illustrates structure and construction of plasmid pFB-CMV-InBar(SV40)-GFP, which comprises a CMV promoter operably linked upstream to a barnase coding sequence that has an inserted SV40 large T antigen intron (SV40) and is fused in-frame with a GFP coding sequence (FIG. 9).

To insert the SV40 large T antigen intron into barnase and construct pFB-CMV-inBar(SV40)-GFP (FIG. 9), a PCR method was employed. The 5'-portion of the barnase coding sequence together with a full-length SV40 large T-antigen intron was PCR amplified from a SV40 plasmid (pUCSV40-B2E, ATCC, Manassas, Va.) with forward primer 5'-CCCCGAATTCGCCACCATGGCACAGG-TATTTGCTTCTTCCTTAAA-3' (SEQ ID NO: 17) (italic typeface indicates the EcoRI restriction site; bold typeface indicates SV40 large T-antigen intron sequence) and reverse primer 5'-TGTTGATAACCTAAAATACACAAACAATTA-3' (SEQ ID NO: 18) (bold typeface indicates SV40 large T-antigen intron sequence). The 3'-portion of the barnase coding sequence together with GFP coding sequence was PCR amplified with forward primer 5'-TGTATTTTAGGT-TATCAACACGTTTGACGG-3' (SEQ ID NO: 19) (bold typeface indicates SV40 large T-antigen intron sequence), and the reverse primer 5'-GGGGGGTACCTCATTACTTG-TACAGCTCGTCC-3' (SEQ ID NO: 20) with pFB-CMV-Bar-GFP as template A second PCR was performed to join these two PCR fragments together with the forward primer 5'-CCCCGAATTCGCCACCATGGCACAGG-TATTTGCTTCTTCCTTAAA-3' (SEQ ID NO: 21) and the reverse primer 5'-GGGGGGTACCTCATTACTTGTA-CAGCTCGTCC-3' (SEQ ID NO: 22). The joined PCR fragment was digested with restriction endonucleases EcoRI and KpnI and ligated to the EcoRI and KpnI sites of pFB-CMV-inDTA (hGH) to replace the DTA sequence and create pFB-CMV-inBar(SV40)-GFP.

Example 6

Figure 10:
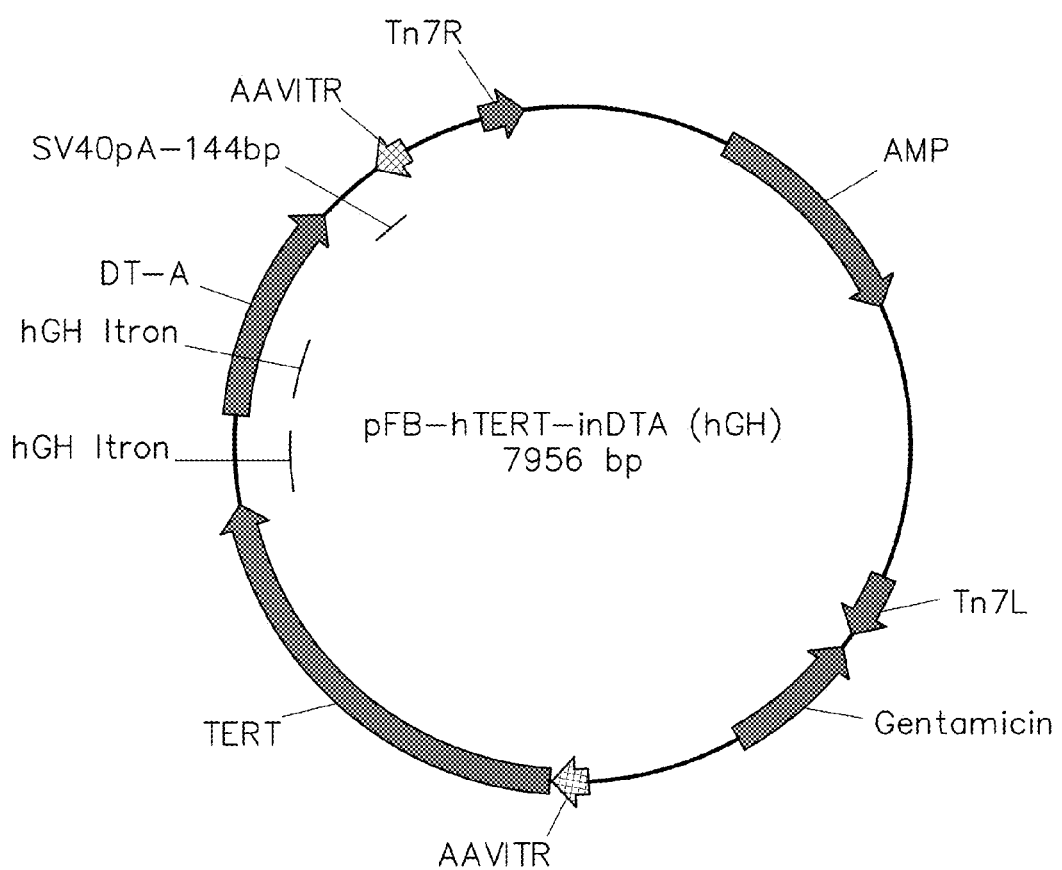

This example illustrates structure and construction of plasmid pFB-hTERT-inDTA (hGH) which comprises a human telomerase reverse transcriptase promoter (hTERT) operably linked upstream to a DT-A coding sequence with an inserted human grow hormone intron (FIG. 10).

To construct pFB-hTERT-inDTA (hGH) (FIG. 10), hTERT was amplified using PCR from genomic DNA purified from human embryonic kidney HEK293 cells with forward primer 5'-GCGCACGCGTATCATCAGCTTTTCAAAGAC-3' (SEQ ID NO: 23) (italic typeface indicates restriction site for MluI) and reverse primer 5'-CGCGACCGGTCGCTGCCT-GAAACTCGCGCC-3' (SEQ ID NO: 24) (italic typeface indicates restriction site for AgeI). The PCR fragment was digested with MluI and AgeI and ligated to the MluI and AgeI sites of pFB-CMV-inDTA (hGH) to create pFB-hTERT-inDTA (hGH).

Example 7

Figure 11:
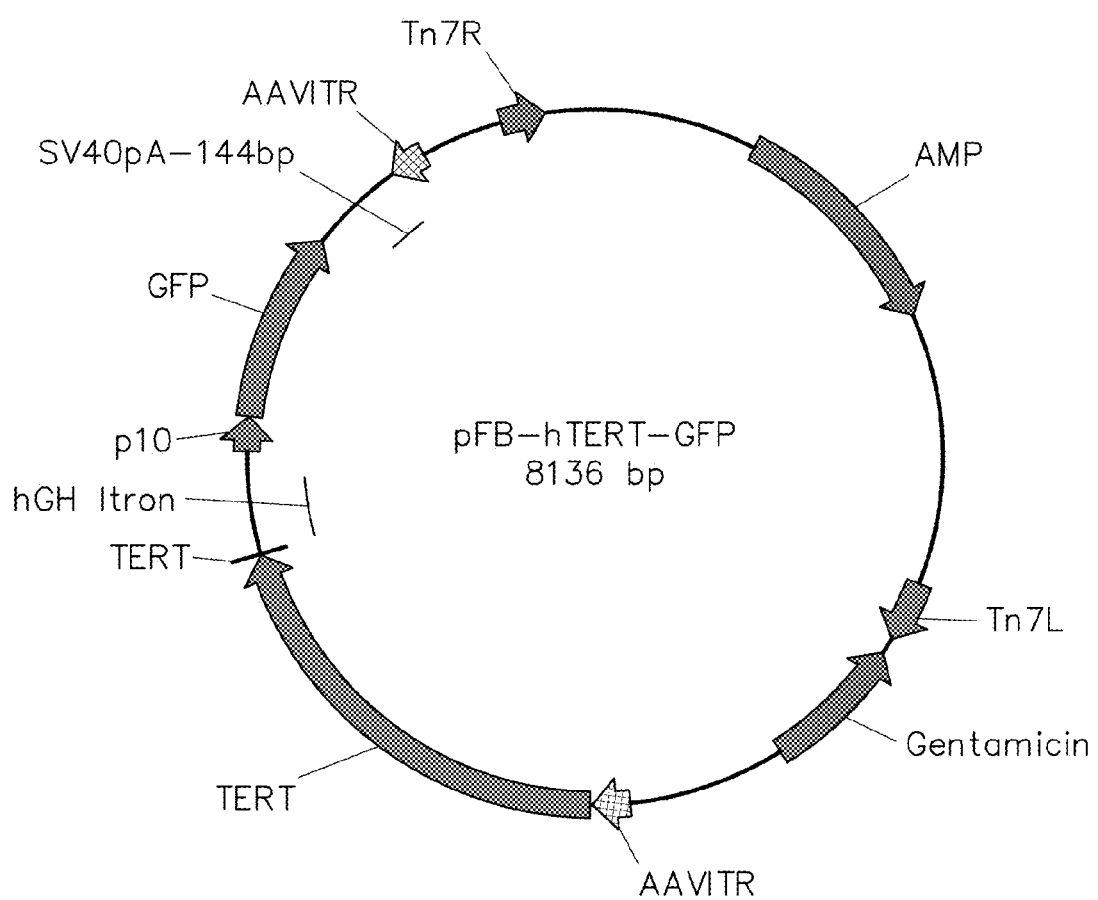

This example illustrates structure and construction of plasmid pFB-hTERT-GFP (hGH) which comprises a human telomerase reverse transcriptase promoter (hTERT) operably linked upstream to a green fluorescent protein (GFP) coding sequence (FIG. 11).

To construct pFB-hTERT-GFP, pFB-CMV-GFP was digested with restriction endonucleases KpnI and AgeI to remove the CMV promoter, and pFB-hTERT-inDTA (hGH) was also digested with the same restriction enzymes to release a fragment comprising the hTERT promoter. This fragment was ligated into the digested pFB-CMV-GFP (without the CMB promoter) to generate pFB-hTERT-GFPs.

Example 8

This example illustrates production of recombinant baculoviruses.

Figure 12:
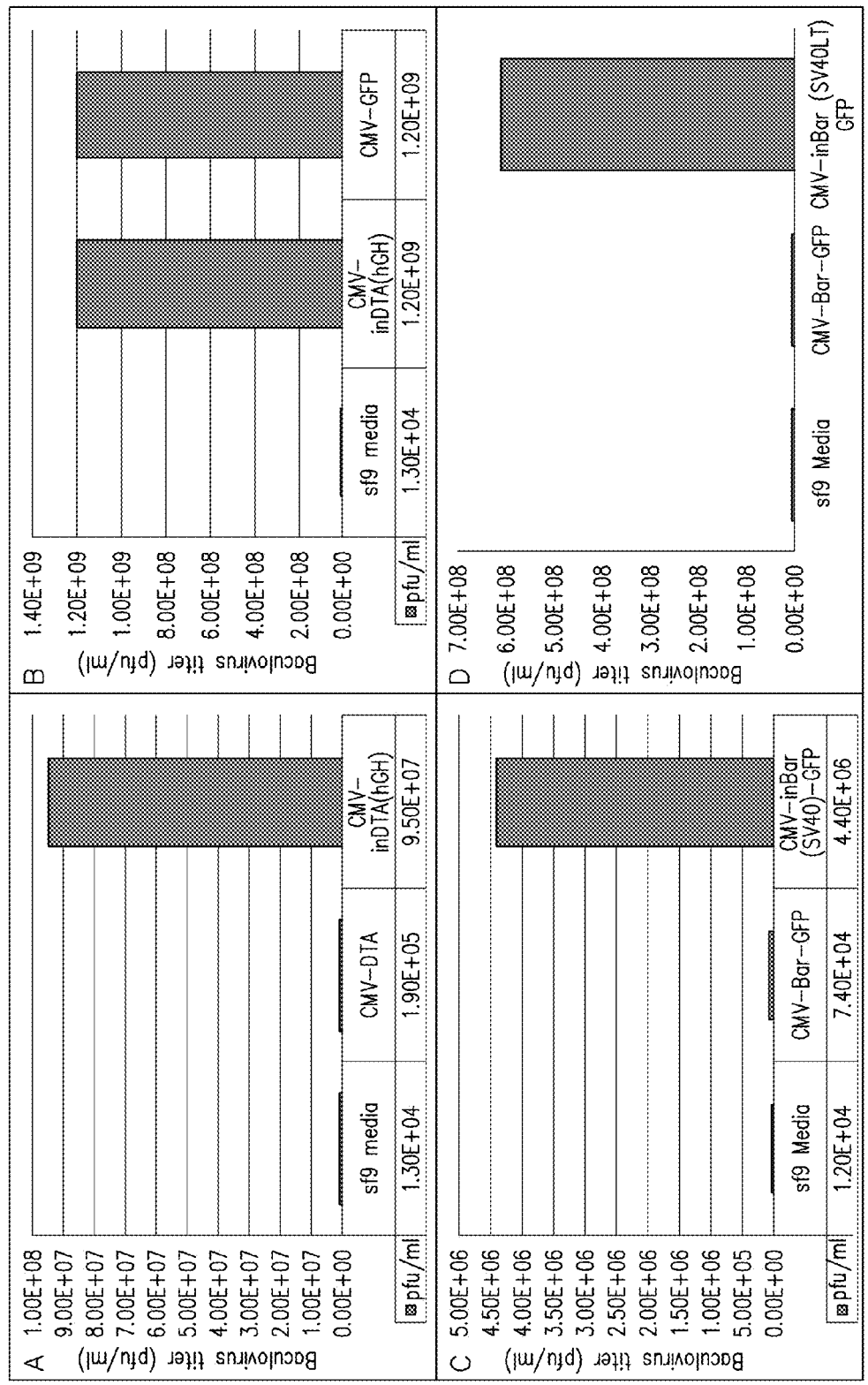
FIG. 12 illustrates generation of recombinant baculoviruses in Sf9 cells following transfection with Bacmid DNA (FIG. 12A, FIG. 12C), and amplification of the recombinant baculoviruses in Sf9 cells by infection (FIG. 12B, FIG. 12D).

In these experiments, toxin-coding sequences with or without intron interruption were cloned into the pFastBac shuttle plasmid as described in Example 3. Schematic depiction of the expression cassettes are shown in FIG. 3. The resultant pFastBac plasmids were used to transform DH10Bac competent bacteria and bacmid DNAs from white colonies were prepared. The bacmid DNAs were used to produce recombinant baculoviruses as described above. The results, as illustrated in FIG. 12, show that no recombinant baculovirus could be generated from the bacmid DNAs containing the DT-A or barnase ORFs without intron insertion, whereas normal levels of recombinant baculoviruses were generated and amplified from the bacmid DNAs containing the DT-A or barnase ORFs interrupted by the mammalian introns. The failure to generate recombinant baculovirus with bacmid DNAs containing the toxin genes without intron interruption demonstrates that DT-A or barnase is lethal to the insect cells even though the toxin genes were under control of the CMV promoter (not an insect promoter). On the other hand, the successful generation and amplification of recombinant baculoviruses from bacmid DNAs containing intron-interrupted toxin genes indicate that both the hGH and SV40LT introns were not spliced in insect cells and therefore no toxins were produced due to the interruption of the DT-A and barnase ORFs.

FIG. 12 shows the generation of recombinant baculoviruses in Sf9 cells by transfection with Bacmid DNA (A & C), and amplification of the recombinant baculoviruses in Sf9 cells by infection (B & D).

In these experiments, baculovirus titers were determined from supernatants harvested 4 days post transfection or 3 days post amplification. CMV-inDTA (hGH), recombinant baculovirus harboring DT-A coding sequence comprising human growth hormone intron (hGH) under control of CMV promoter; CMV-GFP, recombinant baculovirus harboring GFP coding sequence under control of CMV promoter; CMV-Bar-GFP, recombinant baculovirus harboring barnase coding sequence fused in-frame with GFP; CMV-inBar (SV40)-GFP, recombinant baculovirus harboring Barnase coding sequence comprising the SV40 large T-antigen intron and fused in-frame with the GFP coding sequence; CMV-inDTA (hGH), recombinant baculovirus harboring DT-A coding sequence comprising human growth hormone intron (hGH) under control of CMV promoter; CMV-GFP, recombinant baculovirus harboring GFP coding sequence under control of CMV promoter; CMV-Bar-GFP, recombinant baculovirus harboring barnase coding sequence fused in-frame with GFP; CMV-inBar (SV40)-GFP, recombinant baculovirus harboring Barnase coding sequence comprising the SV40 large T-antigen intron and fused in-frame with the GFP coding sequence. Note production of recombinant baculoviruses in insect cells to titers of about $4.4 \times 10^6$ pfu/ml following transfection with CMV-inBaR (SV40)-GFP, or about $9 \times 10^7$ pfu/ml following transfection with pCMV-inDTA (hGH), and production of recombinant baculoviruses in insect cells to titers of about $6.1 \times 10^8$ pfu/ml following infection with CMB-inBar (SV40)-GFP, or about $1.2 \times 10^9$ pfu/ml following infection with either CMV-inDTA (hGH) or CMV-GFP.

Example 9

Figure 2:
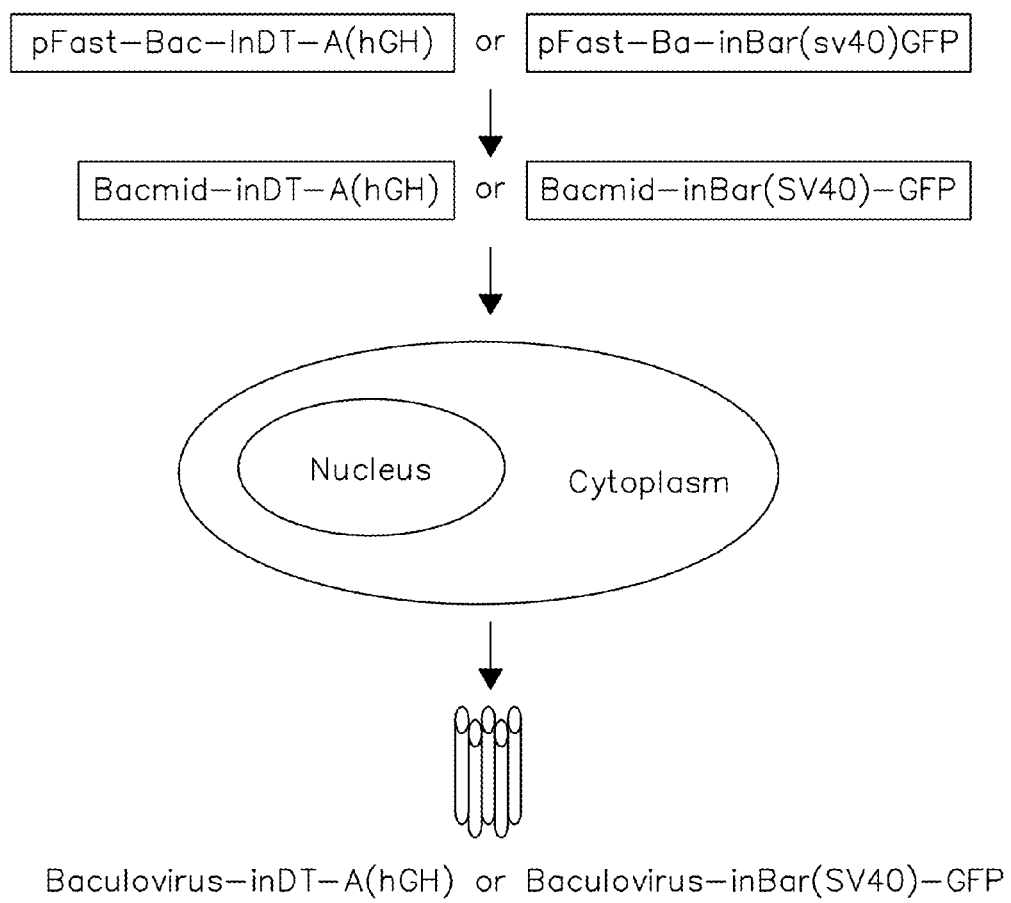
FIG. 2 illustrates a method of producing in an insect cell a recombinant baculovirus carrying a DT-A gene interrupted by the human growth hormone intron or a barnase gene interrupted by the SV40 large T-antigen intron and fused in-frame with GFP.

This example, illustrated in FIG. 2, demonstrates the generation of recombinant baculoviruses carrying DT-A coding sequence comprising an intron.

In these experiments, recombinant baculoviruses were generated according to manufacturer's protocols (Invitrogen). Briefly, the plasmids were respectively diluted into 1 ng/µl in TE buffer and 2 µl of each diluted plasmid was transformed into DH10Bac competent bacteria. After 48-hour incubation, white colonies were picked and miniprep Bacmid DNAs were prepared. The miniprep Bacmid DNAs were respectively transfected into Sf9 cells for 4 days. Cytopathic effect (CPE) was observed for Sf9 cells transfected with bacmids carrying the DT-A gene comprising of the intron, whereas no CPE was observed for Sf9 cells transfected with bacmids carrying the DT-A gene regardless of whether the Tet repressor expression cassette is present or not. These results indicate that any cells transfected with Bacmid carrying DT-A toxic gene was killed off and no recombinant baculovirus was generated and no CPE was observed. Supernatants from all the transfected Sf9 cells were harvested as baculovirus stocks and baculovirus titers were determined with quantitative real-time PCR method using primers corresponding to the baculovirus gp64 gene. The recombinant baculoviruses from those showing apparent CPE were amplified and titers were determined. To determine the titer, recombinant baculoviruses were respectively diluted in 2×TE buffer, and heated at 95° C. for 30 min to break the viral particles and release viral DNA molecules. After cool down to room temperature, the baculoviral samples were diluted with QPCR dilution buffer and assayed with QPCR method with forward primer 5'-CCCTCTGTGTACTTGGCTCTAACG-3' (SEQ ID NO: 25) and reverse primer 5'-CGGTGAAACG-CAAAGTCGAGCACCG-3' (SEQ ID NO: 26). The QPCR titers (genome copies/ml) were converted to plaque forming units (pfu/ml) by dividing with a factor of 20 (empirically determined). The baculovirus titers are shown in the Table 1 below, and FIG. 12. The results demonstrate that recombinant baculoviruses carrying the DT-A gene comprising the human grow hormone intron or the Barnase gene comprising SV40 large T-antigen intron can be generated to high titers, whereas no recombinant baculovirus was generated from bacmids carrying the DT-A gene or the Barnase gene without an intron insertion. The successful generation and amplification of recombinant baculoviruses containing the intron-interrupted toxin ORFs indicate that the mammalian introns were not spliced in insect cells.

Although it is not an insect promoter, CMV promoter has some activity in insect cells and is able to drive low level of hemagglutinin expression (He, F, et al., *BMC Microbiol* 8: 238, 2008). This low level of promoter activity could drive some basal expression of DT-A, which killed any insect cells that express the toxin. No recombinant baculovirus could be produced from bacmid DNA containing the DT-A ORF flanked with loxP sites in an antisense direction to the CMV promoter, indicating that even cryptic promoter TATA-like sequence of the loxP site was able to drive trace amount of DT-A expression that can kill the insect cells. The same phenomenon was observed for the barnase gene, in which recombinant baculoviruses could be generated only when its ORF was interrupted by the SV40LT antigen intron (FIG. 12c), indicating that barnase is also toxic to insect cells. On the other hand, the successful generation of recombinant baculoviruses harboring the intron-interrupted DT-A or the barnase-GFP genes indicates that hGH and SV40LT antigen introns were not spliced in the insect cells and DT-A and barnase-GFP expression was totally abolished by this intron-interruption.

TABLE 1

The titers of recombinant baculoviruses determined by QPCR method

| Sample | Description | Titer (pfu/ml) |
|---|---|---|
| 1 | Negative control, supernatant harvested from Sf9 cell culture | 1.3E+5 |
| 2 | Bac-CMV-DTA, supernatant harvested 4 days post transfection | 1.9E+5 |
| 3 | Bac-CMVtetO-DTA-p10-TetR, supernatant harvested 4 days post transfection | 8.3E+4 |
| 4 | Bac-CMV-inDTA, supernatant harvested 4 days post transfection | 9.5E+7 |
| 5 | Bac-CMVtetO-inDTA-p10-TetR, supernatant harvested 4 days post transfection | 1.1E+8 |
| 6 | Bac-CMV-inDTA, supernatant harvested after one round of amplification | 1.2E+9 |
| 7 | Bac-CMVtetO-inDTA-p10-TetR, supernatant harvested after one round of amplification | 9.7E+8 |
| 8 | Bac-CMV-GFP (control), one round of amplification | 1.2E+9 |

Example 10

This example illustrates splicing of the introns from the toxin ORFs carried by recombinant baculoviruses and expression of the toxin proteins in mammalian cells.

In order to determine if the introns inserted in the toxin ORFs could be spliced out in mammalian cells, recombinant baculoviruses harboring the intron-interrupted DT-A or barnase genes were used to transduce into HEK293 cells. The cell morphology was examined and photographed 2 days after the transduction.

In these experiments, human HEK 293 cells were cultured in DMEM media supplemented with 10% FBS and 100 units/ml of penicillin and 100 µg/ml of streptomycin (Invitrogen, Carlsbad, Calif.) until confluent. The cells were then trypsinized and plated in 24-well plates at 1.5e+5 cell/well in the serum-containing media. After growing overnight, the media were removed and replaced with 250 µl media plus 250 µl recombinant baculovirus, or 400 µl media plus 100 µl recombinant baculovirus. A negative control was performed in the same way except that Sf9 cell culture media were used.

Figure 13:
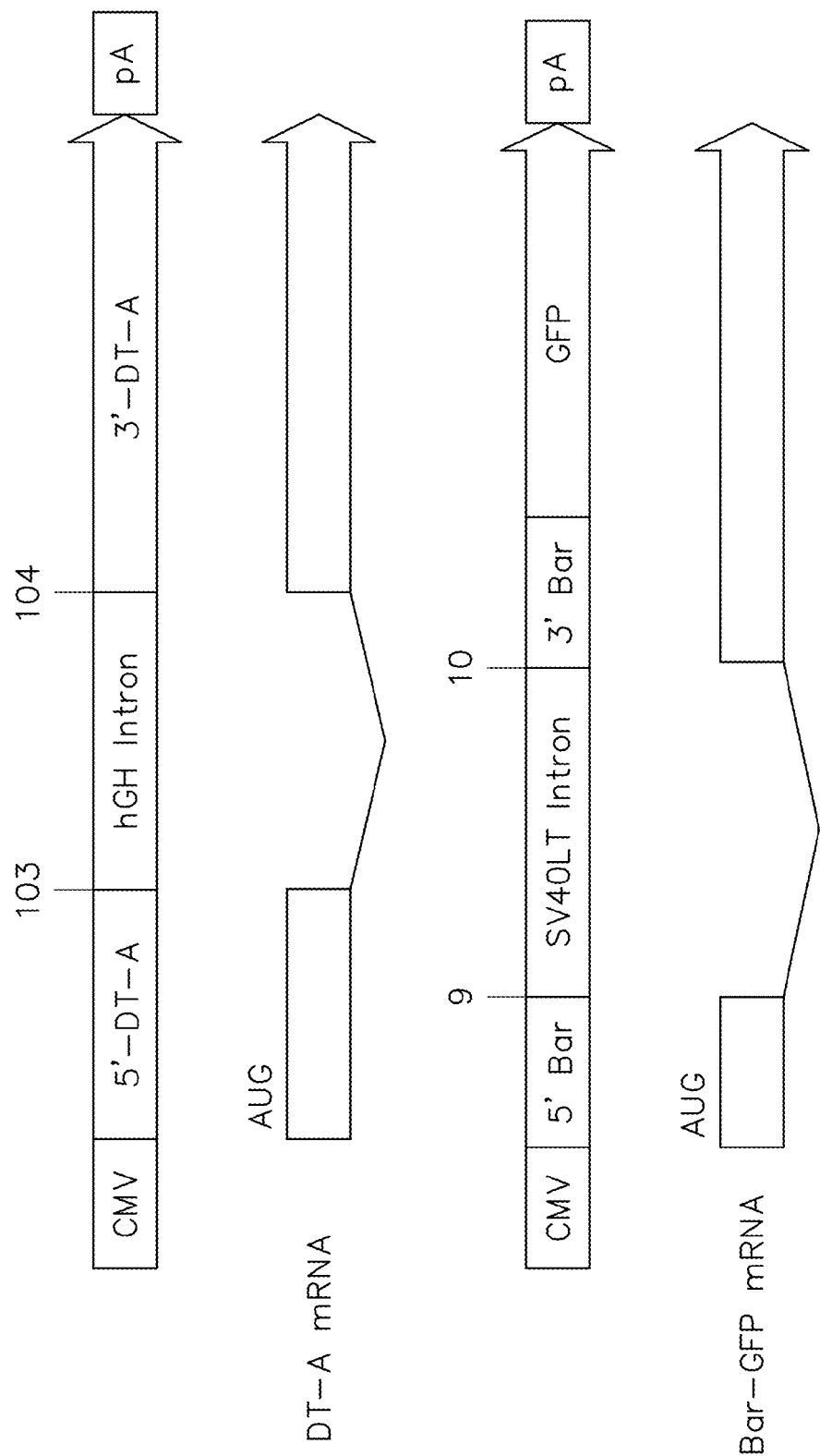
FIG. 13 illustrates genetic and transcriptional maps of representative recombinant baculoviruses carrying a DT-A gene interrupted by a human growth hormone intron, and a Barnase gene interrupted by an SV40 large T-antigen intron and fused in-frame with GFP.

FIG. 13 presents genetic and transcriptional maps of representative recombinant baculoviruses carrying a DT-A gene comprising a human growth hormone intron, and a barnase gene comprising a SV40 large T-antigen intron and fused in-frame with GFP. Upon introduction into a mammalian cell, mature DT-A mRNA or Bar-GFP mRNA is formed through intron splicing and translated into fully functional DT-A or Barnase protein to kill the cell. The numbers above the genetic maps based on DT-A and Barnase coding sequences indicate the nucleotide positions where the introns were inserted.

Figure 14:
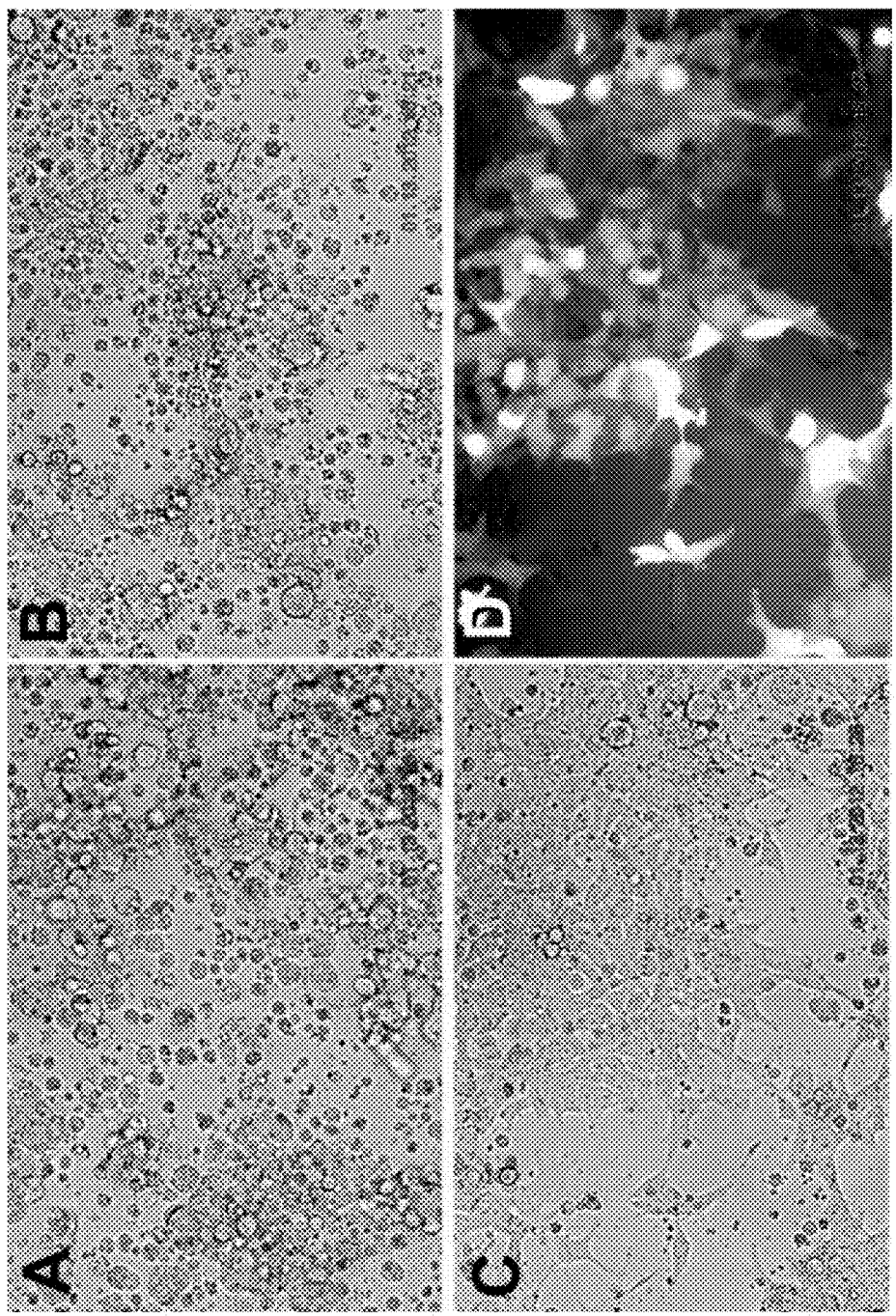
FIG. 14 illustrates the killing effects on mammalian (human embryonic kidney HEK293) cells by transduction with recombinant baculoviruses harboring toxic genes for 48 hours.

In these experiments, following introduction of a barnase gene comprising an intron into mammalian cells and incubation for another 3 days, the cells were examined under microscope and CPE of the cells was recorded. Results are shown in Table 2 and FIG. 14. FIG. 14 illustrates the killing effects on mammalian (human embryonic kidney HEK293) cells by transduction with recombinant baculoviruses harboring toxic genes for 48 hours. A, B, and C: representative fields photographed with a 20× objective lens under bright field illumination using a tungsten light source. D: Same field as in C, imaged by fluorescence illumination using a filter combination with excitation and transmission wavelengths suitable for GFP fluorescence. A, Bac-CMV-inDTA (hGH); B, Bac-CMV-inBar (SV40)-GFP; C, Bac-CMV-GFP; D, same image as C showing GFP expression. The results in FIG. 14 show that recombinant baculoviruses carrying either intron-interrupted DT-A or barnase genes caused fragmentation of HEK293 cells, a typical sign of cells undergoing apoptosis, whereas recombinant baculoviruses carrying GFP gene did not cause this fragmentation. In the 293 cells transduced with baculovirus carrying Bar-GFP, very faint GFP expression was observed (data not shown). Whether transduced by 100 µl or 250 µl of the recombinant baculoviruses carrying the DT-A gene comprising the hGH intron, or a barnase gene comprising a SV40 large T-antigen intron, most of the HEK 293 cells were rounded up and loosely detached, displaying heavy CPE, whereas all HEK 293 cells transduced with recombinant baculovirus carrying GFP did not show any sign of CPE and were growing as well as the negative control. These results demonstrate that in mammalian HEK293 cells, the introns (hGH intron or SV40 large T-antigen intron) were spliced out and DT-A mRNA or barnase-GFP mRNA were formed and translated, so that the host cells expressed functional DT-A or Barnase-GFP-fusion proteins, thereby killing the host HEK293 cells.

TABLE 2

Expression of DT-A in human HEK293 cells through baculovirus transduction

| Sample | Description | Volume added (µl) | CPE observed |
|---|---|---|---|
| 1 | ESF921 media | 100 | − |
| 2 | ESF921 media | 250 | − |
| 3 | Baculovirus Bac-CMV-GFP | 100 | − |
| 4 | Baculovirus Bac-CMV-GFP | 250 | − |
| 5 | Baculovirus Bac-CMV-inDTA | 100 | ++++ |
| 6 | Baculovirus Bac-CMV-inDTA | 250 | ++++ |
| 7 | Baculovirus Bac-CMVtetO-inDTA-p10-TetR | 100 | ++++ |
| 8 | Baculovirus Bac-CMVtetO-inDTA-p10-TetR | 250 | ++++ |

Example 11

This example illustrates production of AAV vectors harboring the toxin ORFs in insect cells.

Figure 15:
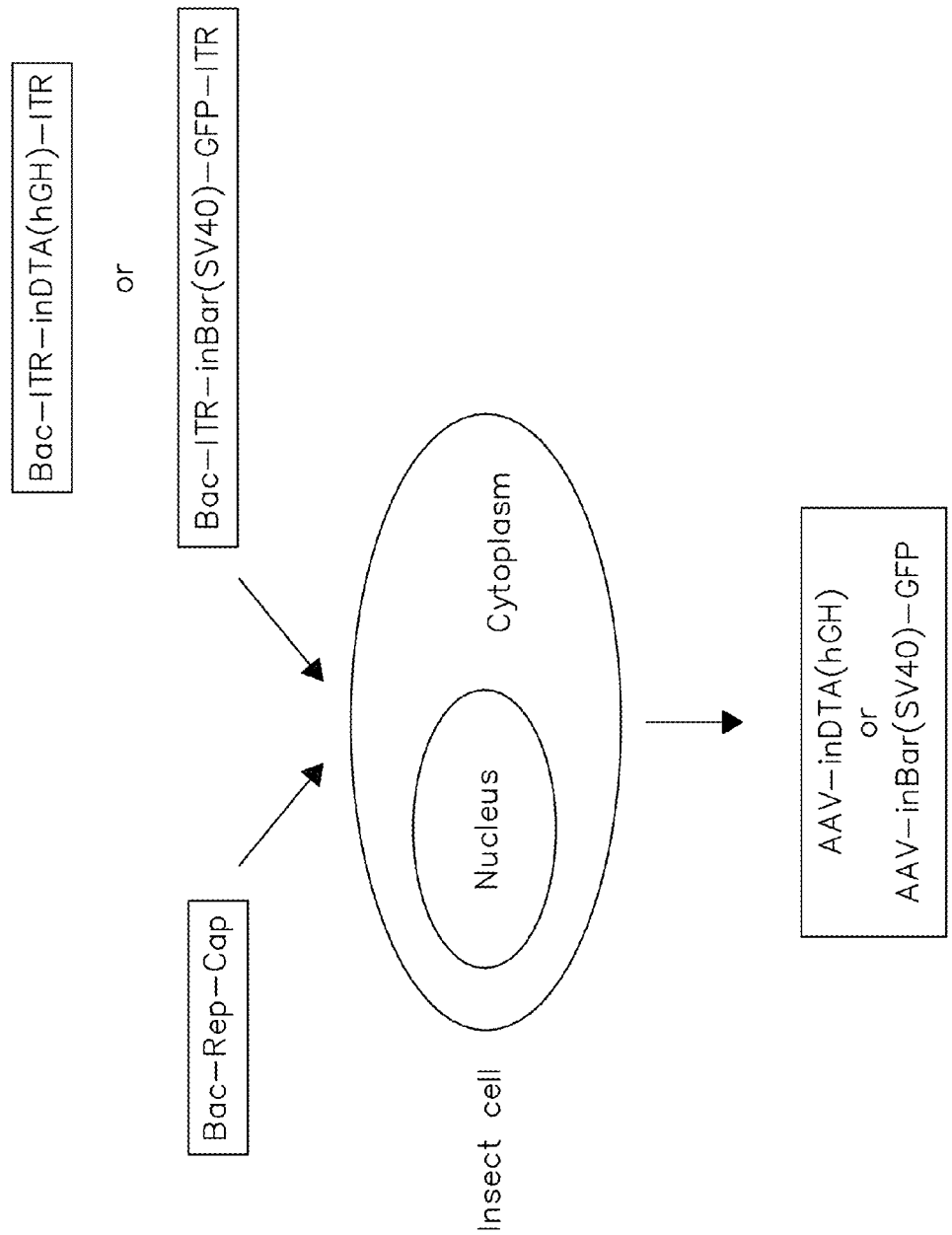
FIG. 15 illustrates a method of producing AAV vectors carrying a DT-A gene comprising the human growth hormone intron or the barnase gene comprising the SV40 large T-antigen intron and fused in-frame with GFP gene in insect cells that carries a stably integrated AAV-transgene.
Figure 16:
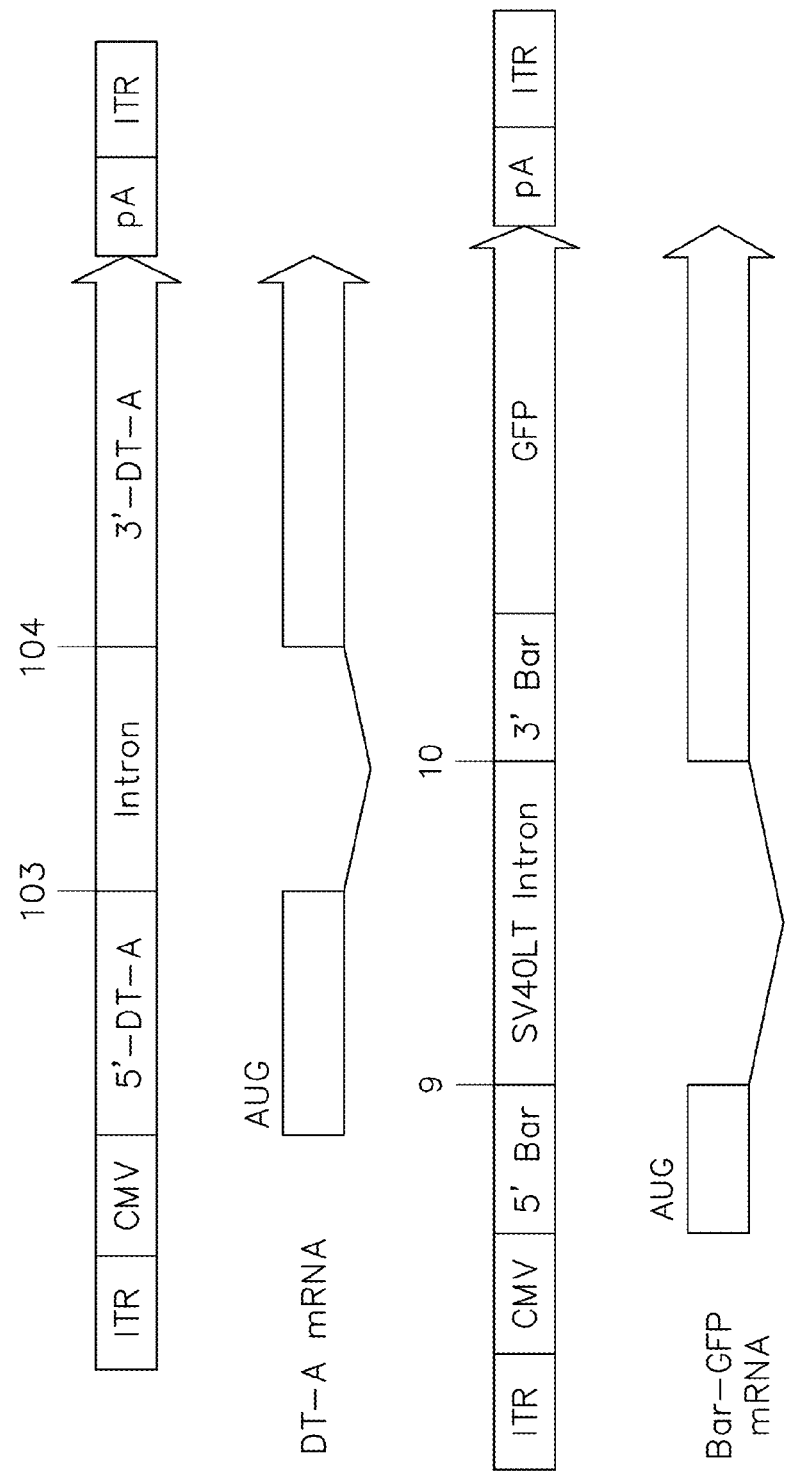
FIG. 16 illustrates genetic and transcriptional maps of representative AAV vectors carrying a DT-A gene comprising a human growth hormone intron, or a Barnase gene comprising a SV40 large T-antigen intron and fused in-frame with the GFP gene.

In these experiments, the production of AAV vectors carrying the DT-A gene comprising the human growth hormone intron or the Barnase gene comprising the SV40 large T-antigen intron and fused in-frame with GFP gene in insect cells (FIG. 15, FIG. 16). FIG. 15 illustrates a method of producing AAV vectors carrying a DT-A gene comprising the human growth hormone intron or the barnase gene comprising the SV40 large T-antigen intron and fused in-frame with GFP gene in insect cells that carries a stably integrated AAV-transgene. FIG. 16 illustrates genetic and transcriptional maps of representative AAV vectors carrying a DT-A gene comprising a human growth hormone intron, or a Barnase gene comprising a SV40 large T-antigen intron and fused in-frame with the GFP gene. The numbers above the genetic maps based on the DT-A coding sequence and the Barnase coding sequence indicate the nucleotide positions where the introns were inserted.

AAV vector production was performed in Sf9 cells with the recombinant baculoviruses harboring intron-interrupted toxin ORFs. The recombinant baculoviruses were used to co-infect Sf9 cells with a second recombinant baculovirus expressing AAV Rep and Cap genes for 3 days and AAV vectors were purified and titrated. The results in Tables 3 and 4 show that very similar yields of AAV vectors carrying the intron-interrupted toxin ORFs were produced as compared to AAV vectors carrying just the GFP gene.

In these experiments, Sf9 cells were grown to about 1E+9 cells/ml in ESF921 media (Expression Systems, CA) supplemented with 100 units/ml of penicillin and 100 µg/ml of streptomycin. The cells were then diluted 1:1 with fresh media and infected with 10 moi of Bac-RepCap9 and 5 moi of Bac-CMV-inDTA or Bac-CMVtetO-inDTA-p10-TetR for 3 days. The cell pellets were harvested by centrifugation at 2000 rpm for 10 min. and lysed in SF9 lysis buffer (50 mM Tris-HCl, pH 7.4, 2 mM $MgCl_2$, 1% sarkosyl, 1% triton X-100, 125 units/ml of benzonase). Cellular DNA was digested by incubating at 37 C for 60 min. Cell lysates were cleared by centrifugation at 8000 rpm for 30 min. and loaded onto an SW28 centrifuge tubes containing 5 ml of 1.55 g/cc, and 10 ml of 1.32 g/cc of CsCl solutions. After centrifugation at 28,000 rpm for about 16 hours at 15° C., the rAAV-containing fraction was collected by puncturing the centrifuge tube using a syringe needle and subjected to a second round of CsCl ultracentrifugation. The rAAV-containing fraction was collected again by puncturing the centrifuge tube using a syringe needle and dialyzed in PBS buffer to remove the salts and detergents. Vector titers were determined by quantitative real-time PCR assay according to manufacturer's protocol (Applied Biosystems, Foster City, Calif.). The results, presented in Table 3 and table 4, show that high titers of rAAV vectors carrying the toxic DT-A gene can be produced in Sf9 cells using the recombinant baculovirus that carries the DT-A gene comprising an intron with or without tet suppression, indicating that the insertion of an intron is required for AAV vector production.

TABLE 3

Production of AAV vectors carrying DT-A gene

| Sample | Description | Total yield (vg/liter culture) | Relative yield (%) |
|---|---|---|---|
| 1 | AAV9-CMV-GFP (control vector) | 6.63E+14 | 100 |
| 2 | AAV9-CMV-inDTA (hGH) | 7.53E+14 | 114 |
| 3 | AAV9-CMVtetO-inDTA | 5.32E+14 | 80 |

TABLE 4

Production of AAV9 and AAV2 vectors carrying the DT-A gene comprising the human growth hormone intron or the Barnase gene comprising the SV40 large T-antigen intron

| Sample | Description | Total yield (vg/liter culture) |
|---|---|---|
| 1 | AAV9-CMV-GFP (control vector) | 6.63E+14 |
| 2 | AAV9-CMV-inDTA | 7.53E+14 |
| 3 | AAV2-CMV-GFP (hGH) (control vector) | 1.15E+15 |
| 4 | AAV2-CMV-inDTA (hGH) | 1.15E+15 |
| 5 | AAV2-CMV-inBar(SV40)-GFP | 6.58E+14 |
| 6 | AAV2-hTERT-inDTA(hGH) | 9.30E+14 |

These results confirm that the mammalian introns were not functional in insect cells, which resulted in the successful production of AAV vectors that carry the intron-interrupted toxin ORFs. In addition, both AAV2 and AAV9 vectors were produced at similar yields, indicating that this AAV vector production was universal and not serotype specific.

Example 12

This example illustrates non-specific killing by AAV vectors containing DT-A under control of CMV promoter.

Figure 17A:
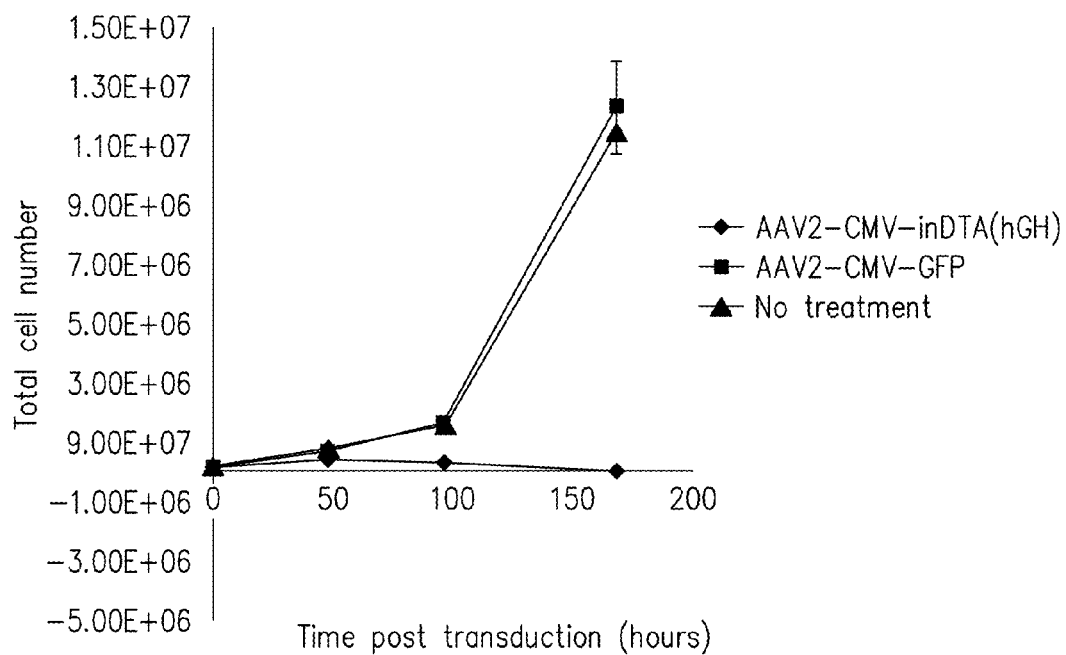
FIG. 17 illustrates the killing effect of AAV2-CMV-inDTA (hGH) on mammalian cells.
Figure 17B:
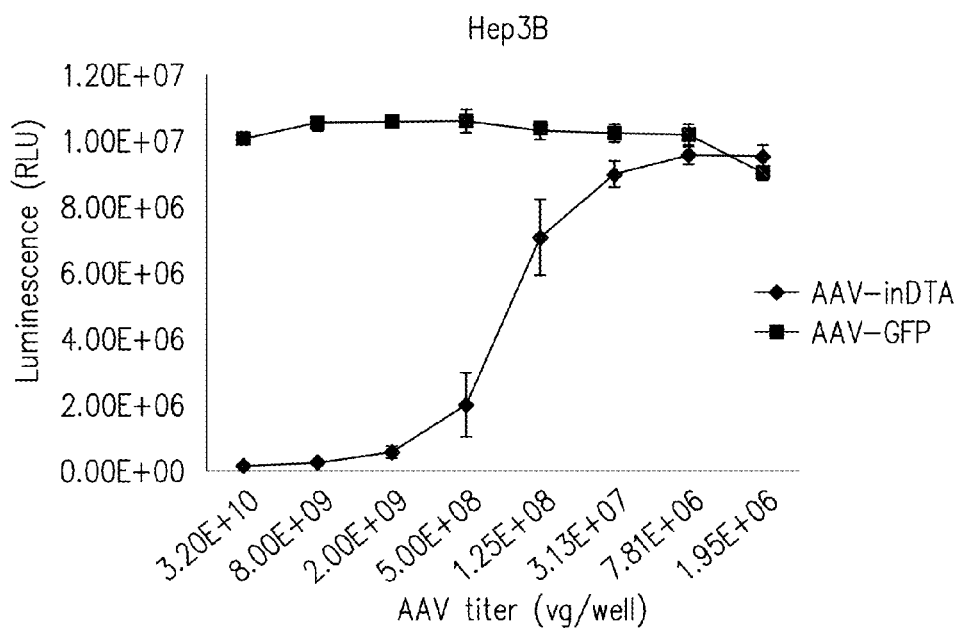

Since recombinant baculoviruses harboring the intron-interrupted toxin genes were able to kill the mammalian cells through transduction, we examined whether the AAV vectors harboring the toxin genes could also exert the killing effect on HEK293 cells. To test this possibility, HEK293 cells were plated on 24-well plates overnight and transduced with the AAV2 and AAV9 vectors. The results show that after transduction for 48 hours, the HEK293 cells transduced with either AAV2 or AAV9 vectors carrying DTA or barnase gene displayed fragmented cellular morphology, a typical phenomenon of cells undergoing apoptosis. In contrast, there was no sign of apoptosis in the cells transduced with AAV2 or 9 vectors carrying the GFP gene (data not shown). These results demonstrate that the introns were spliced out from the toxin coding sequences to form mature mRNAs and the mRNAs were translated into toxin proteins that killed the HEK293 cells. Since AAV2 exhibits much better in vitro transduction efficiency than AAV9, it was chosen for further in vitro experiments. A cell proliferation assay was performed on HEK293 cells to further confirm the cell killing effect and the results are shown in FIG. 17a. The HEK293 cells transduced with AAV2-CMV-inDTA (hGH) were inhibited with no signs of growth, whereas the cells transduced with AAV2-CMV-GFP grew as well as the untreated ones. Further, a cell viability assay was performed to verify the cytotoxicity of AAV2-CMV-inDTA (hGH) on Hep3B cells. The results are shown in FIG. 17b. A nice dose-response curve was observed. With the decrease of AAV2 vectors carrying DTA, the cell viability increased, whereas there was essentially no change of cell viability for AAV2-CMV-GFP treated cells.

FIG. 17 illustrates the killing effect of AAV2-CMV-inDTA (hGH) on mammalian cells. (a) Proliferation of 293 cells transduced with AAV2 vectors. The cells (1.5E+5 cells/well) were seeded in a 24-well plate overnight and transduced with AAV2-CMV-inDTA(hGH), or AAV2-CMV-GFP. The cell numbers were counted at different time points. When they reached confluency, the cells were split into a larger culture areas and let grow. (b) The viability of Hep3B cells transduced with AAV2 vectors. Hep3B cells (3.2E+4 cells/well) were seeded in a 96-well plate overnight and transduced with a 4-fold serial dilution of AAV2-CMV-GFP, or AAV2-CMV-inDTA(hGH). The cell viability was determined with CellTiter Glo Luminescent Cell Viability Assay Kit (Promega).

Figure 18:
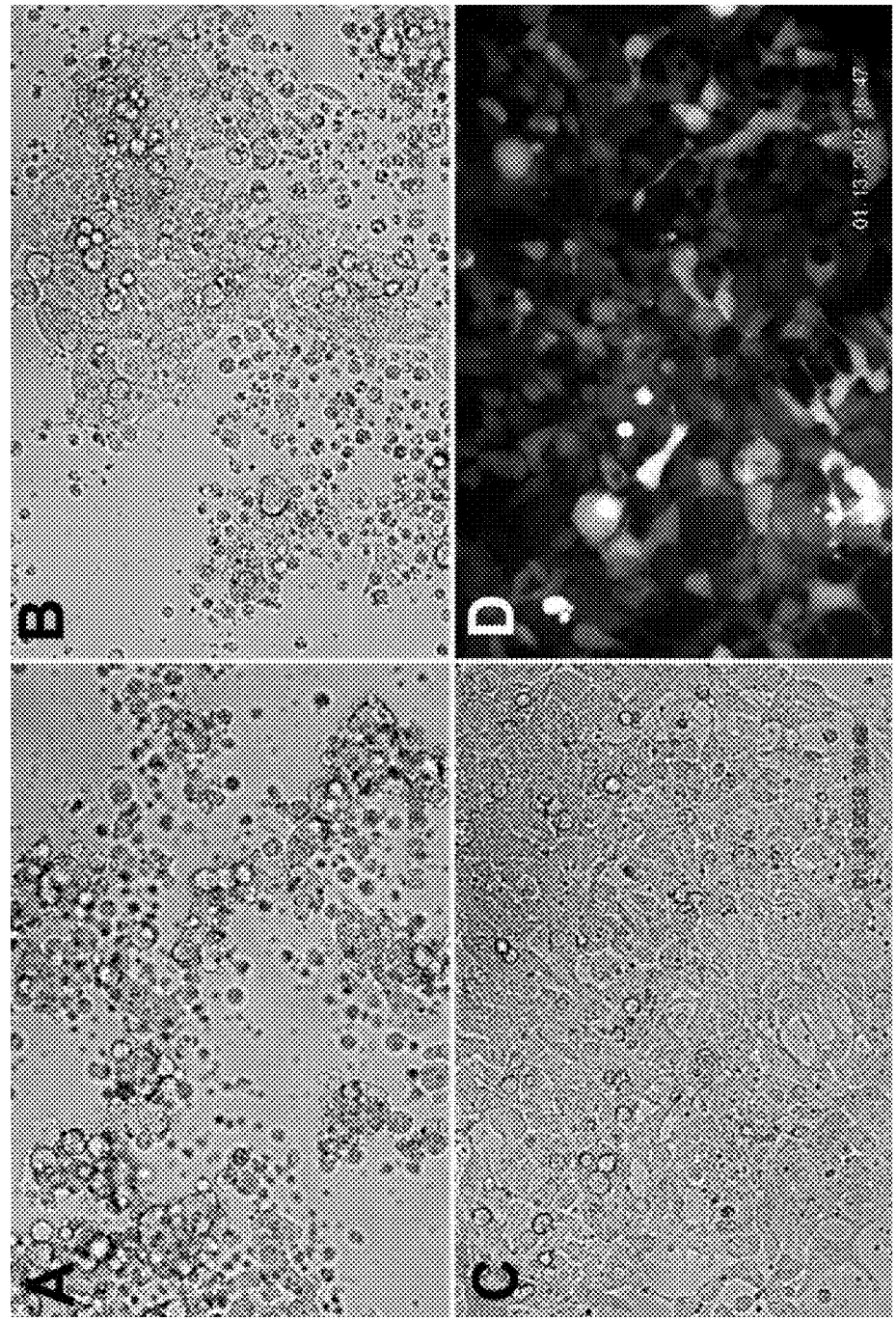
FIG. 18 illustrates the killing effects on mammalian cells by transduction with AAV vectors harboring toxic genes.

FIG. 18 illustrates the killing effects on human HEK293 cells by transduction with AAV vectors harboring toxic genes for 48 hours. The images were photographed with 20× lens under tungsten lighting (A, B, and C) or fluorescent lighting (D). A, AAV2-CMV-inDTA(hGH); B, AAV2-CMV-inBar (SV40)-GFP; C, AAV2-CMV-GFP; D, same image as C showing GFP expression.

In these experiments, HEK 293 cells harboring an AAV with CMV-inDTA(hGH) or CMV-inBar(SV40)-GFP were rounded up and loosely detached, displaying heavy CPE. However, all HEK 293 cells transduced with recombinant baculovirus carrying GFP did not show any sign of CPE, and were growing as well as the negative control. These results demonstrate that in these mammalian cells, the introns (hGH intron or SV40 large T-antigen intron) were spliced out and DT-A mRNA or barnase-GFP mRNA were formed and translated, and the host cells expressed functional DT-A or Barnase-GFP-fusion proteins, thereby killing the host HEK293 cells.

Example 13

This example illustrates production of an AAV vector comprising DT-A gene with the reading frame interrupted with an intron, under the control AFP enhancer and promoter sequences.

In these experiments, the human AFP enhancer and promoter sequences were both PCR amplified from genomic DNA purified from human embryonic kidney HEK293 cells. The AFP enhancer was amplified with forward primer 5'-CCGCACGCGTCTTAGAAATATGGGGG-TAGGGGTGG-3' (SEQ ID NO: 27) (italic typeface indicates restriction site for MluI) and reverse primer 5'-CT-CAAACTCTAGTGGCCTGGATAAAGCTGAGTG-3' (SEQ ID NO: 28). The AFP promoter was amplified with forward primer 5'-CTTTATCCAGGCCACTA-GAGTTTGAGGAGAATATTTG-3' (SEQ ID NO: 29) and reverse primer 5'-ACTTACCTGACCGGTTGCTAGT-TATTTTGTTAT-3' (SEQ ID NO: 30). The two PCR fragments were joined together by a second PCR amplification with the forward primer for the AFP enhancer and the reverse primer for the AFP promoter as described above. The final PCR fragment was digested with MluI and AgeI and ligated to the MluI and AgeI sites of pFB-CMV-inDTA (hGH) to replace the CMV promoter and create pFB-hAFP-inDTA (hGH).

AAV2-hAFP-inDTA (hGH) was produced in insect cells by methods described herein to a titer of 1.69E+15.

Example 14

This example illustrates production of an AAV vector comprising DT-A gene with the reading frame interrupted with an intron, under the control the human survivin (SURV) promoter sequence.

In these experiments, the human survivin (SURV) promoter sequence was PCR amplified with genomic DNA purified from human embryonic kidney HEK293 cells with forward primer 5'-GGGGACTAGTCTGGCCATAGAACCA-GAGAAGTGA-3' (SEQ ID NO: 31) (italic typeface indicates restriction site for SpeI) and reverse primer 5'-TTTTACCG-GTCCACCTCTGCCAACGGGTCCCGCG-3' (SEQ ID NO: 32) (italic typeface indicates restriction site for AgeI). The PCR fragment was digested with SpeI and AgeI and ligated to the SpeI and AgeI sites of pFB-CMV-inDTA (hGH) to replace the CMV promoter and create pFB-hSURV-inDTA (hGH).

AAV2-hSURV-inDTA (hGH) was produced in insect cells by methods described herein to a titer of 1.41E+15 vg/liter culture.

Example 15

This example illustrates production of an AAV vector comprising DT-A gene with the reading frame interrupted with an intron, under the control the human cyclooxygenase-2 (COX2) promoter sequence.

In these experiments, the human cyclooxygenase-2 (COX2) promoter was PCR amplified with genomic DNA purified from human embryonic kidney HEK293 cells with forward primer 5'-GCCCACTAGTTGAGGTACCTGGTG-TAGTTT-3' (SEQ ID NO: 33) (italic typeface indicates restriction site for SpeI) and reverse primer 5'-ATATACCG-GTCAGCGGCGGGCAGGGCGCGG-3' (SEQ ID NO: 34) (italic typeface indicates restriction site for AgeI). The PCR fragment was digested with SpeI and AgeI and ligated to the SpeI and AgeI sites of pFB-CMV-inDTA (hGH) to replace the CMV promoter and create pFB-hCOX2-inDTA (hGH).

AAV2-hCOX2-inDTA (hGH) was produced in insect cells by methods described herein to a titer of 2.22E+13 vg/liter culture.

Example 16

This example illustrates production of an AAV vector comprising DT-A gene with the reading frame interrupted with an intron, under the control the human cholecystokinin type-A receptor (CCKAR) promoter sequence (Takata, Y., et al., J. Gastroenterol. 37: 815-820, 2002).

In these experiments, the human cholecystokinin type-A receptor (CCKAR) promoter sequence was PCR amplified with genomic DNA purified from human embryonic kidney HEK293 cells with forward primer 5'-GCCCACTAGTAC-CCAGGTACCTATGTTCAAAAG-3' (SEQ ID NO: 35) (italic typeface indicates restriction site for SpeI) and reverse primer 5'-GCGCACCGGTTTGCCTGCTGCTTTCCAC-CAAG-3' (SEQ ID NO: 36) (italic typeface indicates restriction site for AgeI). The PCR fragment was digested with SpeI and AgeI and ligated to the SpeI and AgeI sites of pFB-CMV-inDTA (hGH) to replace the CMV promoter and create pFB-hCCKAR-inDTA (hGH).

AAV2-hCCKAR-inDTA (hGH) was produced in insect cells by methods described herein to a titer of 1.96E+14 vg/liter culture.

Example 17

This example illustrates production of an AAV vector comprising DT-A gene with the reading frame interrupted with an intron, under the control the human CXCR4 gene promoter sequence (Caruz, M., et al, FEBS Letters, 426: 271-278, 1998).

In these experiments, the human CXCR4 promoter sequence was PCR amplified with genomic DNA purified from human embryonic kidney HEK293 cells with forward primer 5'-GCCCACTAGTTACCGACCACCCGCAAA-CAG-3' (SEQ ID NO: 37) (italic typeface indicates restriction site for SpeI) and reverse primer 5'-GCGCACCGGTG-TAACCGCTGGTTCTCCAGA-3' (SEQ ID NO: 38) (italic typeface indicates restriction site for AgeI). The PCR fragment was digested with SpeI and AgeI and ligated to the SpeI and AgeI sites of pFB-CMV-inDTA (hGH) to replace the CMV promoter and create pFB-hCXCR4-inDTA (hGH).

AAV2-hCXCR4-inDTA (hGH) was produced in insect cells by methods described herein to a titer of 1.81E+15 vg/liter culture.

Example 18

This example illustrates tumor-specific killing by AAV vectors carrying DT-A under control of tumor-specific promoters.

In these experiments, cells were seeded on 24-well plates and transduced with AAV2 vectors carrying DT-A under control of various tumor-specific promoters as described above.

Figure 19A:
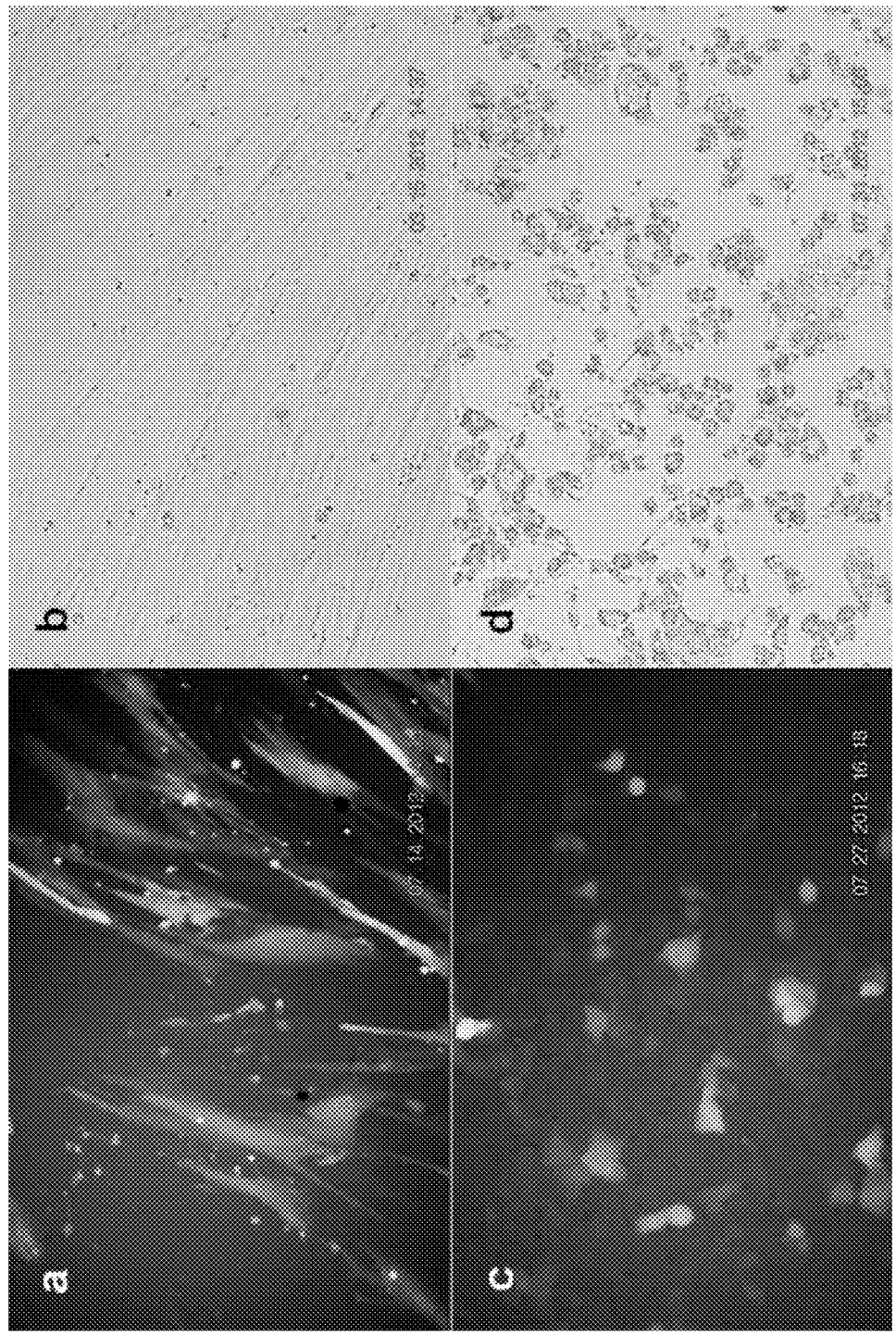
FIG. 19 illustrates representative result of cell killing by AAV2-hSURV-inDTA(hGH).

The results indicate that neuroblastoma BE(2)-M17 cells were killed by DT-A under control of hSURV or hCXCR4 but not hAFP promoter, whereas hepatocellular carcinoma Hep3B and HepG2 cells were killed by DT-A under control of either AFP, SURV, or CXCR4 promoters. The normal human lung cell line WI38 was not affected by DT-A under control of AFP, SURV, or hTERT promoter. FIG. 19 illustrates representative results of cell killing by AAV2-hSURV-inDTA (hGH). In these experiments, the cells were seeded in 24-well plate and transduced with AAV2-CMV-GFP (a), (c), (e), and (g) or AAV2-hSURV-inDTA(hGH) (b), (d), (f), and (h). Photographs were taken 3 days post transduction. (a) & (b), WI38; (c) and (d), HepG2; (e) and (f), Hep3B, and (g) and (h), BE(2)-M17 cells.

Figure 20A:
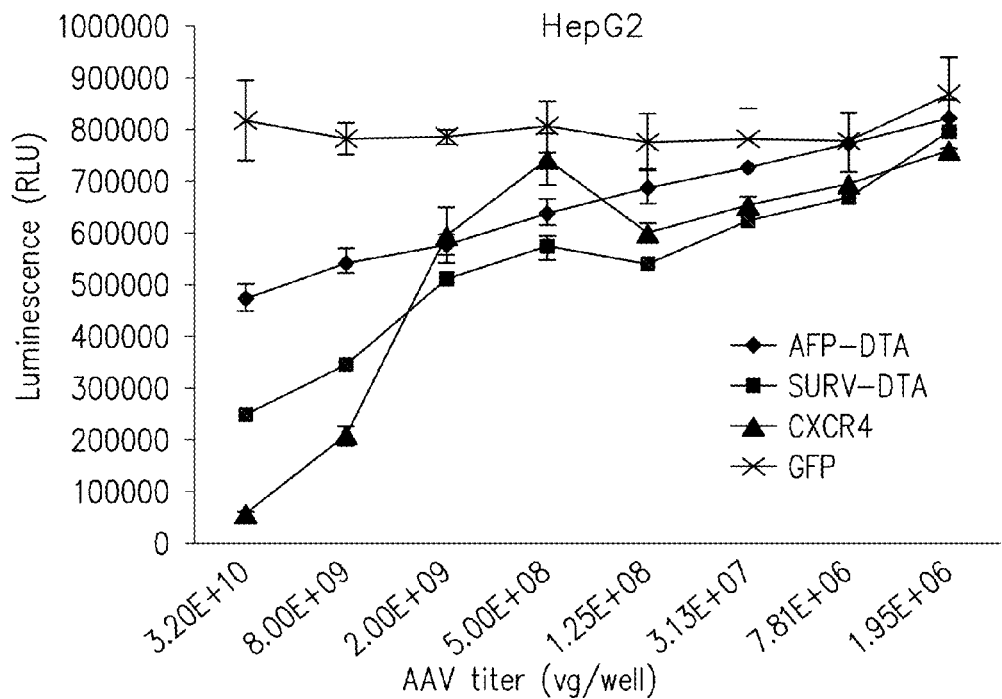
FIG. 20 illustrates cell viability assay of tumor cells by AAV2 vectors carrying DT-A under control of various tumor-specific promoters. The cells were seeded on 96-well plates and transduced with AAV2 vectors at 4-fold serial dilutions for 4 days and the cell viability was assayed with the CellTiter Glo Luminescent Cell Viability Assay kit. (a) HepG2 cells, (b) Hep3B cells, and (c) BE(2)-M17 cells.
Figure 20B:
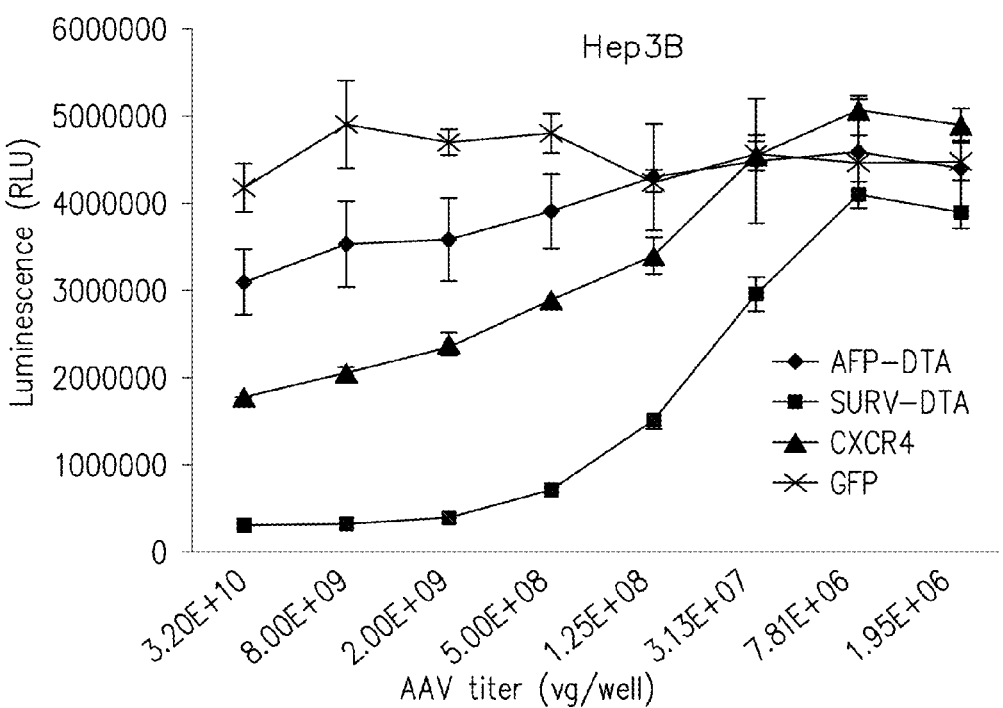
Figure 20C:
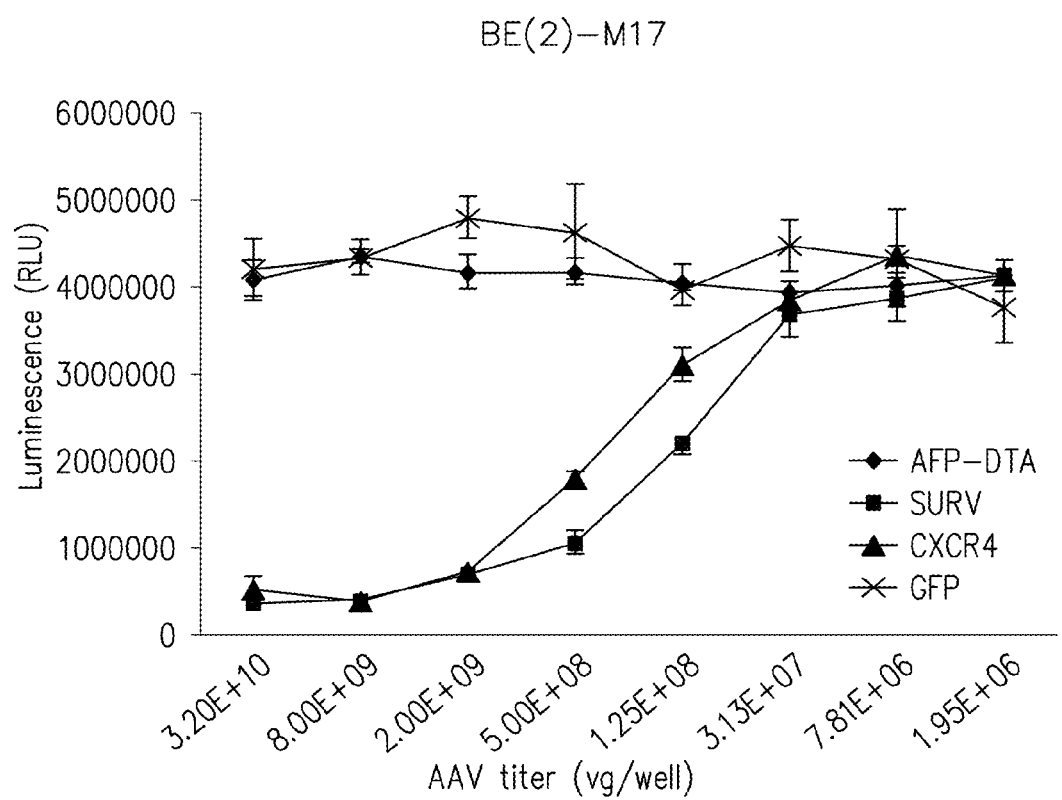

The three tumor cell lines were also tested with DTA under control of human COX2, CCKAR, and hTERT promoters but no significant cell killing effect was observed. In order to further characterize the cell killing effects, the cell viability assays were performed with DTA under control of AFP, SURV, and CXCR4 promoters. FIG. 20 illustrates cell viability assay of tumor cells by AAV2 vectors carrying DT-A under control of various tumor-specific promoters. In these experiments, the cells were seeded on 96-well plates and transduced with AAV2 vectors at 4-fold serial dilutions for 4 days and the cell viability was assayed with the CellTiter Glo Luminescent Cell Viability Assay kit. (a) HepG2 cells, (b) Hep3B cells, and (c) BE(2)-M17 cells. All three tumor-specific promoters show transcription activity in HepG2 cells. Among which the CXCR4 promoter exhibited the highest activity driving DTA to kill HepG2 cells when high titers of AAV2 vectors were used (FIG. 20a). For Hep3B cells, DTA under control of the SURV promoter exhibited the strongest killing effect, whereas AFP and CXCR4 showed partial killing activities (FIG. 20b). Interestingly, AFP promoter was not active in BE(2)-M17 cells, whereas DTA under control of both CXCR4 and SURV promoters exhibited strong killing effects (FIG. 20c).

All publications, including patent applications, patents, and other references mentioned herein are incorporated by reference, each in its entirety. Any discussion of references cited herein is intended merely to summarize the assertions made by their authors and no admission is made that any reference or portion thereof constitutes relevant prior art. Applicant reserves the right to challenge the accuracy and pertinency of the cited references.

What is claimed is:

1. A nucleic acid comprising:
a sequence encoding a toxic polypeptide; and
an intron that interrupts the sequence, whereby the intron is spliced in mammalian cells but not in insect cells to form an mRNA that is translated to form cell-toxic levels of the toxic polypeptide in mammalian cells but not in insect cells.

2. A nucleic acid in accordance with claim 1, wherein the toxic polypeptide is selected from the group consisting of diphtheria toxin (DT-A), barnase, ricin, abrin, and Pseudomonas exotoxin.

3. A nucleic acid in accordance with claim 1, wherein the toxic polypeptide is diphtheria toxin (DT-A).

4. A nucleic acid accordance with claim 1, wherein the toxic polypeptide is a barnase polypeptide.

5. A nucleic acid in accordance with claim 1, further comprising at least one expression element operably linked to the sequence.

6. A nucleic acid in accordance with claim 5, wherein the expression element is selected from the group consisting of a promoter, an IRES, an enhancer and a combination thereof.

7. A nucleic acid in accordance with claim 5, wherein the expression element is selected from the group consisting of a CMV promoter, an AFP promoter, an AFT enhancer, an hSURV promoter, a CXCR4 promoter, an hTERT promoter, a COX2 promoter, and a CCKAR promoter.

8. A nucleic acid in accordance with claim 5, wherein the expression element is selected from the group consisting of an hSURV promoter and a CXCR4 promoter.

9. A nucleic acid in accordance with claim 1, wherein the intron is an artificial intron.

10. A nucleic acid in accordance with claim 1, wherein the intron is selected from the group consisting of a human growth hormone intron and a SV40 large T-antigen intron.

11. A nucleic acid in accordance with claim 1, comprising, in 5' to 3' order, a first ITR, a promoter, a first portion of a toxic gene, an intron, a second portion of the toxic gene, a polyadenylation signal, and a second ITR.

12. A nucleic acid in accordance with claim 11, wherein the first ITR is an AAV ITR.

13. A nucleic acid in accordance with claim 11, wherein the second ITR is an AAV ITR.

14. A nucleic acid in accordance with claim 11, wherein the promoter is selected from the group consisting of a CMV promoter, a hSURV promoter, a hCXCR4 promoter, and a hAFP promoter.

15. A nucleic acid in accordance with claim 11, wherein toxic gene encodes DT-A.

16. A nucleic acid in accordance with claim 11, wherein the toxic gene encodes Barnase.

17. A viral vector comprising the nucleic acid of claim 1, wherein the vector is selected from the group consisting of a baculovirus, a retrovirus, an adenovirus, an adeno-associated virus (AAV) and a combination thereof.

18. A viral vector in accordance with claim 17, wherein the vector is a baculovirus, an adeno-associated virus (AAV), or a combination thereof.

19. A viral vector in accordance with claim 17, wherein the vector is an adeno-associated virus (AAV).

20. A viral vector in accordance with claim 17, wherein the vector is selected from the group consisting of an AAV2 and an AAV9.

21. An insect cell in vitro comprising the nucleic acid of claim 1.

22. An insect cell in accordance with claim 21, wherein the nucleic acid is comprised by a viral genome.

23. An insect cell in accordance with claim 21, wherein the cell is stably transformed with the nucleic acid of claim 1.

24. A cell culture comprising:
a plurality of cells of claim 21; and
a culture medium.

25. A cell culture in accordance with claim 24, wherein unconcentrated culture medium comprises a baculovirus greater than $10^6$ PFU/ml.

26. A method of growing a vector comprising a toxic gene in vitro, comprising:
providing a cell culture comprising insect cells;
infecting or transfecting the cells with a nucleic acid of claim 1; and
incubating the cells under conditions suitable for virus production.

* * * * *